US007618780B2

(12) United States Patent
Thompson

(10) Patent No.: US 7,618,780 B2
(45) Date of Patent: Nov. 17, 2009

(54) USE OF MASS LABELLED PROBES TO DETECT TARGET NUCLEIC ACIDS USING MASS SPECTROMETRY

(75) Inventor: Andrew Thompson, Cambridge (GB)

(73) Assignee: Trillion Genomics Limited, Cambridge (GB)

(*) Notice: Subject to any disclaimer, the term of this patent is extended or adjusted under 35 U.S.C. 154(b) by 30 days.

(21) Appl. No.: 11/597,109

(22) PCT Filed: May 19, 2005

(86) PCT No.: PCT/GB2005/001980

§ 371 (c)(1),
(2), (4) Date: Nov. 20, 2006

(87) PCT Pub. No.: WO2005/113804

PCT Pub. Date: Dec. 1, 2005

(65) Prior Publication Data

US 2007/0292861 A1 Dec. 20, 2007

Related U.S. Application Data

(60) Provisional application No. 60/572,464, filed on May 20, 2004.

(51) Int. Cl.
*C12Q 1/68* (2006.01)
*C07H 21/02* (2006.01)
*C07H 21/04* (2006.01)
(52) U.S. Cl. .................... 435/6; 536/23.1; 536/24.3
(58) Field of Classification Search .......... 435/6; 536/23.1, 24.3
See application file for complete search history.

(56) References Cited

U.S. PATENT DOCUMENTS

| | | | |
|---|---|---|---|
| 4,988,617 A | 1/1991 | Landegren et al. | |
| 5,538,848 A * | 7/1996 | Livak et al. ............ | 435/6 |
| 5,599,660 A | 2/1997 | Ramanujam et al. | |
| 5,618,701 A | 4/1997 | Landegren | |
| 5,652,107 A | 7/1997 | Lizardi et al. | |
| 5,759,773 A | 6/1998 | Tyagi et al. | |
| 5,759,784 A | 6/1998 | Asp et al. | |
| 5,854,033 A | 12/1998 | Lizardi | |
| 5,871,921 A | 2/1999 | Landegren et al. | |
| 5,952,201 A | 9/1999 | Landegren et al. | |
| 6,030,787 A * | 2/2000 | Livak et al. ............ | 435/6 |
| 6,183,960 B1 | 2/2001 | Lizardi | |
| 6,210,884 B1 | 4/2001 | Lizardi | |
| 6,235,472 B1 | 5/2001 | Landegren et al. | |
| 6,287,824 B1 | 9/2001 | Lizardi | |
| 6,291,669 B1 | 9/2001 | Kwiatkowski et al. | |
| 6,313,284 B1 | 11/2001 | Kwiatkowski et al. | |
| 6,344,329 B1 | 2/2002 | Lizardi | |
| 6,429,309 B1 | 8/2002 | Kwiatkowski et al. | |
| 6,558,928 B1 | 5/2003 | Landegren | |
| 6,635,452 B1 * | 10/2003 | Monforte et al. ........ | 506/9 |
| 6,858,412 B2 * | 2/2005 | Willis et al. ............ | 435/91.1 |
| 6,878,515 B1 | 4/2005 | Landegren | |
| 7,074,564 B2 | 7/2006 | Landegren | |
| 7,306,904 B2 | 12/2007 | Landegren et al. | |
| 7,320,860 B2 | 1/2008 | Landegren et al. | |
| 7,351,528 B2 * | 4/2008 | Landegren ............. | 435/6 |
| 2002/0150927 A1* | 10/2002 | Matray et al. ........... | 435/6 |
| 2004/0038234 A1* | 2/2004 | Gut et al. .............. | 435/6 |
| 2004/0058349 A1* | 3/2004 | Van Ness et al. ........ | 435/6 |
| 2005/0100939 A1* | 5/2005 | Namsaraev et al. ...... | 435/6 |
| 2005/0147973 A1* | 7/2005 | Knott .................. | 435/6 |
| 2005/0250147 A1* | 11/2005 | Macevicz .............. | 435/6 |

FOREIGN PATENT DOCUMENTS

| | | |
|---|---|---|
| JP | 4262799 | 9/1992 |
| JP | 4304900 | 10/1992 |
| WO | WO01/68664 | 9/2001 |
| WO | WO02/057491 | 7/2002 |
| WO | WO03/020734 A2 * | 3/2003 |
| WO | WO03/025576 | 3/2003 |

OTHER PUBLICATIONS

Fu et al. Sequencing exons 5 to 8 of the p53 gene by MALDI-TOF mass spectrometry. Nature Biotechnology 16 : 381-384 (1998).*
Stoerker et al., Rapid genotyping by MALDI-monitored nuclease selection from probe libraries. Nature Biotechnology 18 : 1213-1216 (2000).*
Paul Hardenbol, et al., Multiplexed Genotyping with Sequence-Tagged Molecular Inversion Probes, Nature Biotechnology, Jun. 2003, pp. 673-678, vol. 21, No. 6, Nature Publishing Group, http://www/nature.com/naturebiotechnology.
Johan Baner, et al., Parallel Gene Analysis with Allele-Specific Padlock Probes and Tag Microarrays, Nucleic Acids Research, 2003, pp. 1-7, vol. 31, No. 17 e103, Oxford University Press, DOI:10.1093/nar/gng104.
Mats Nilsson, et al., Enhanced Detection and Distinction of RNA by Enzymatic Probe Ligation, Nature Biotechnology, Jul. 2000, pp. 791-793, vol. 18, Nature America Inc., http://biotech.nature.com.
Mats Nilsson, et al., RNA-Templated DNA Ligation for Transcript Analysis, Nucleic Acids Research, 2001, pp. 578-581, vol. 29, No. 2, Oxford University Press.

(Continued)

Primary Examiner—Ethan Whisenant
(74) Attorney, Agent, or Firm—Barbara A. Wrigley; Oppenheimer Wolff & Donnelly, LLP

(57) ABSTRACT

The invention relates to the use of mass labelled probes to characterize nucleic acids by mass spectrometry. Thus the invention provides methods of detecting the presence of a target nucleic acid in a sample, using a circularizing probe in which a mass tag is present in the probe. Further methods of detecting the presence of a target nucleic acid are provided, which in contrast use a probe detection sequence in the circularizing probe, wherein the probe detection sequence is detected with a probe attached to a mass tag. Methods for determining a genetic profile from the genome of an organism also form part of the invention.

7 Claims, 8 Drawing Sheets

OTHER PUBLICATIONS

Johan Baner, et al., Signal Amplification of Padlock Probes by Rolling Circle Replication, Nucleic Acids Research, 1998, pp. 5073-5078, vol. 26, No. 22, Oxford University Press.

Paul M. Lizardi, et al., Mutation Detection and Single-Molecule Counting Using Isothermal Rolling-Circle Amplification, Nature Genetics, Jul. 1998, pp. 225-232, vol. 19, Nature America Inc., http://genetics.nature.com.

Heiko Kuhn, et al., Rolling-Circle Amplification Under Topological Constraints, Nucleic Acids Research, 2002, vol. 30, No. 2, pp. 574-580, Oxford University Press,.

Anders Isaksson, et al., Accessing Genomic Information: Alternatives to PCR, Current Opinion in Biotechnology, 1999, vol. 10, pp. 11-15, Elsevier Science Ltd ISSN 0958-1669, http://biomednet.com/elecref/0958166901000011.

Marianna Szemes, et al., Diagnostic Application of Padlock Probes-Multiplex Detection of Plant Pathogens Using Universal Microarrays, Nucleic Acids Research, Apr. 2005, vol. 33, No. 8 e70, pp. 1-13, Oxford University Press, doi:10.1093/nar/gni069.

Fredrik Dahl, et al., Multiplex Amplification Enabled by Selective Circularization of Large Sets of Genomic DNA Fragments, Nucleic Acids Research, Apr. 2005, vol. 33, No. 8 e71, pp. 1-7, Oxford University Press, doi:10.1093/nar/gni070.

Mats Nilsson, et al., Real-Time Monitoring of Rolling-Circle Amplification Using a Modified Molecular Beacon Design, Nucleic Acids Research, 2002, vol. 30, No. 14 e66, pp. 1-7, Oxford University Press,.

Olle Ericsson, et al., A Dual-Tag Microarray Platform for High-Performance Nucleic Acid and Protein Analyses, Nucleic Acids Research, Mar. 2008, pp. 1-9, Nucleic Acids Research Advance Access, doi:10.1093/nar/gkn106.

Ann-Christine Syvanen, et al., Enthusiasm Mixed with Scepticism About Single-Nucleotide Polymorphism Markers for Dissecting Complex Disorders, European Journal of Human Genetics, 1999, vol. 7, pp. 98-101, Stockton Press, http://www.stockton-press.co.uk/ejhg.

Johan Baner, et al., More Keys to Padlock Probes: Mechanisms for High-Throughput Nucleic Acid Analysis, Current Opinion in Biotechnology, 2001, vol. 12, pp. 11-15, Elsevier Science Ltd.

Fawad A. Faruqi, et al., High-Throughput Genotyping of Single Nucleotide Plymorphisms with Rolling Circle Amplification, BMC Genomics, Aug. 2001, 2:4, BioMed Central Ltd., http://www.biomedcentral.com/1471-2164/2/4.

D.-O. Antson, et al., PCR-Generated Padlock Probes Detect Single Nucleotide Variation in Genomic DNA, Nucleic Acids Research, 2000, vol. 28, No. 12, e58, pp. 1-6, Oxford University Press.

David C. Thomas, et al., Amplification of Padlock Probes for DNA Diagnostics by Casca eRolling Circle Amplification or the Polymerase Chain Reaction, Arch Pathol Lab Med, Dec. 1999, vol. 123, pp. 1170-1176, Oncor, Inc.

* cited by examiner

Inject solute into ESI-MS and detect Mass Tags

SEQUENCE LISTING

<160> NUMBER OF SEQ ID NOS: 43

<210> SEQ ID NO 1

-continued

```
<211> LENGTH: 15
<212> TYPE: DNA
<213> ORGANISM: Artificial sequence
<220> FEATURE:
<223> OTHER INFORMATION: 5prime Target Recognition Sequence

<400> SEQUENCE: 1
atgtattgat agata                                                          15

<210> SEQ ID NO 2
<211> LENGTH: 20
<212> TYPE: DNA
<213> ORGANISM: Artificial sequence
<220> FEATURE:
<223> OTHER INFORMATION: Primer binding sequence

<400> SEQUENCE: 2
atgttaagtg accggcagca                                                     20

<210> SEQ ID NO 3
<211> LENGTH: 20
<212> TYPE: DNA
<213> ORGANISM: Artificial sequence
<220> FEATURE:
<223> OTHER INFORMATION: Probe Identification Sequence

<400> SEQUENCE: 3
gatttgatta gatttggtaa                                                     20

<210> SEQ ID NO 4
<211> LENGTH: 15
<212> TYPE: DNA
<213> ORGANISM: Artificial sequence
<220> FEATURE:
<223> OTHER INFORMATION: 3prime Target Recognition Sequence

<400> SEQUENCE: 4
acatataaat catcc                                                          15

<210> SEQ ID NO 5
<211> LENGTH: 15
<212> TYPE: DNA
<213> ORGANISM: Artificial sequence
<220> FEATURE:
<223> OTHER INFORMATION: 5prime Target Recognition Sequence

<400> SEQUENCE: 5
acgtattgat agata                                                          15

<210> SEQ ID NO 6
<211> LENGTH: 20
<212> TYPE: DNA
<213> ORGANISM: Artificial sequence
<220> FEATURE:
<223> OTHER INFORMATION: Probe Identification Sequence

<400> SEQUENCE: 6
agtaatgtga tttgataaag                                                     20

<210> SEQ ID NO 7
<211> LENGTH: 15
<212> TYPE: DNA
<213> ORGANISM: Artificial sequence
<220> FEATURE:
<223> OTHER INFORMATION: 3prime Target Recognition Sequence

<400> SEQUENCE: 7
```

```
acatataaat catca                                              15

<210> SEQ ID NO 8
<211> LENGTH: 70
<212> TYPE: DNA
<213> ORGANISM: Artificial sequence
<220> FEATURE:
<223> OTHER INFORMATION: Linear Circularising Probe 1 (and Linear
      Circularising Probe 3)

<400> SEQUENCE: 8
atgtattgat agataatgtt aagtgaccgg cagcagattt gattagattt ggtaaacata    60
taaatcatcc                                                           70

<210> SEQ ID NO 9
<211> LENGTH: 70
<212> TYPE: DNA
<213> ORGANISM: Artificial sequence
<220> FEATURE:
<223> OTHER INFORMATION: Linear Circularising Probe 2

<400> SEQUENCE: 9
acgtattgat agataatgtt aagtgaccgg cagcaagtaa tgtgatttga taaagacata    60
taaatcatca                                                           70

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
tgctgccggt cacttaacat                                                20

<210> SEQ ID NO 11
<211> LENGTH: 20
<212> TYPE: DNA
<213> ORGANISM: Artificial sequence
<220> FEATURE:
<223> OTHER INFORMATION: Probe Detection Sequence 1

<400> SEQUENCE: 11
gatttgatta gatttggtaa                                                20

<210> SEQ ID NO 12
<211> LENGTH: 20
<212> TYPE: DNA
<213> ORGANISM: Artificial sequence
<220> FEATURE:
<223> OTHER INFORMATION: Probe Detection Sequence 2

<400> SEQUENCE: 12
agtaatgtga tttgataaag                                                20

<210> SEQ ID NO 13
<211> LENGTH: 15
<212> TYPE: DNA
<213> ORGANISM: Artificial sequence
<220> FEATURE:
<223> OTHER INFORMATION: 5prime Target Recognition Sequence

<400> SEQUENCE: 13
ccgtattgat agata                                                     15
```

```
<210> SEQ ID NO 14
<211> LENGTH: 15
<212> TYPE: DNA
<213> ORGANISM: Artificial sequence
<220> FEATURE:
<223> OTHER INFORMATION: 5prime Target Recognition Sequence

<400> SEQUENCE: 14
tcgtattgat agata                                              15

<210> SEQ ID NO 15
<211> LENGTH: 15
<212> TYPE: DNA
<213> ORGANISM: Artificial sequence
<220> FEATURE:
<223> OTHER INFORMATION: 5prime Target Recognition Sequence

<400> SEQUENCE: 15
gcgtattgat agata                                              15

<210> SEQ ID NO 16
<211> LENGTH: 70
<212> TYPE: DNA
<213> ORGANISM: Artificial sequence
<220> FEATURE:
<223> OTHER INFORMATION: Linear Circularising Probe 4

<400> SEQUENCE: 16
acgtattgat agataatgtt aagtgaccgg cagcaagtaa tgtgatttga taaagacata    60
taaatcatca                                                         70

<210> SEQ ID NO 17
<211> LENGTH: 70
<212> TYPE: DNA
<213> ORGANISM: Artificial sequence
<220> FEATURE:
<223> OTHER INFORMATION: Linear Circularising Probe 4

<400> SEQUENCE: 17
ccgtattgat agataatgtt aagtgaccgg cagcaagtaa tgtgatttga taaagacata    60
taaatcatca                                                         70

<210> SEQ ID NO 18
<211> LENGTH: 70
<212> TYPE: DNA
<213> ORGANISM: Artificial sequence
<220> FEATURE:
<223> OTHER INFORMATION: Linear Circularising Probe 4

<400> SEQUENCE: 18
tcgtattgat agataatgtt aagtgaccgg cagcaagtaa tgtgatttga taaagacata    60
taaatcatca                                                         70

<210> SEQ ID NO 19
<211> LENGTH: 70
<212> TYPE: DNA
<213> ORGANISM: Artificial sequence
<220> FEATURE:
<223> OTHER INFORMATION: Linear Circularising Probe 4

<400> SEQUENCE: 19
gcgtattgat agataatgtt aagtgaccgg cagcaagtaa tgtgatttga taaagacata    60
```

```
taaatcatca                                                           70

<210> SEQ ID NO 20
<211> LENGTH: 21
<212> TYPE: DNA
<213> ORGANISM: Artificial sequence
<220> FEATURE:
<223> OTHER INFORMATION: Primer binding sequence 1

<400> SEQUENCE: 20
tgctttccag accgtccatc a                                              21

<210> SEQ ID NO 21
<211> LENGTH: 21
<212> TYPE: DNA
<213> ORGANISM: Artificial sequence
<220> FEATURE:
<223> OTHER INFORMATION: Primer binding sequence 2; and Primer 2.

<400> SEQUENCE: 21
ggtgcctgtg cattgcctgc c                                              21

<210> SEQ ID NO 22
<211> LENGTH: 21
<212> TYPE: DNA
<213> ORGANISM: Artificial sequence
<220> FEATURE:
<223> OTHER INFORMATION: Primer 1

<400> SEQUENCE: 22
gatggacggt ctggaaagca a                                              21

<210> SEQ ID NO 23
<211> LENGTH: 92
<212> TYPE: DNA
<213> ORGANISM: Artificial sequence
<220> FEATURE:
<223> OTHER INFORMATION: Linear Circularising Probe 5

<400> SEQUENCE: 23
atgtattgat agatatgctt tccagaccgt ccatcagatt tgattagatt tggtaaggtg    60
cctgtgcatt gcctgccaca tataaatcat cc                                  92

<210> SEQ ID NO 24
<211> LENGTH: 92
<212> TYPE: DNA
<213> ORGANISM: Artificial sequence
<220> FEATURE:
<223> OTHER INFORMATION: Linear Circularising Probe 6

<400> SEQUENCE: 24
acgtattgat agatatgctt tccagaccgt ccatcaagta atgtgatttg ataaagggtg    60
cctgtgcatt gcctgccaca tataaatcat ca                                  92

<210> SEQ ID NO 25
<211> LENGTH: 20
<212> TYPE: DNA
<213> ORGANISM: Artificial sequence
<220> FEATURE:
<223> OTHER INFORMATION: Probe Detection Sequence 3

<400> SEQUENCE: 25
ttaccaaatc taatcaaatc                                                20
```

```
<210> SEQ ID NO 26
<211> LENGTH: 20
<212> TYPE: DNA
<213> ORGANISM: Artificial sequence
<220> FEATURE:
<223> OTHER INFORMATION: Probe Detection Sequence 4

<400> SEQUENCE: 26
ctttatcaaa tcacattact                                                   20

<210> SEQ ID NO 27
<211> LENGTH: 15
<212> TYPE: DNA
<213> ORGANISM: Artificial sequence
<220> FEATURE:
<223> OTHER INFORMATION: 5prime Target Recognition Sequence

<400> SEQUENCE: 27
tttgtggaga caggt                                                        15

<210> SEQ ID NO 28
<211> LENGTH: 15
<212> TYPE: DNA
<213> ORGANISM: Artificial sequence
<220> FEATURE:
<223> OTHER INFORMATION: 3prime Target Recognition Sequence

<400> SEQUENCE: 28
aatatgtggt cacac                                                        15

<210> SEQ ID NO 29
<211> LENGTH: 15
<212> TYPE: DNA
<213> ORGANISM: Artificial sequence
<220> FEATURE:
<223> OTHER INFORMATION: 3prime Target Recognition Sequence

<400> SEQUENCE: 29
aatatgtggt cacat                                                        15

<210> SEQ ID NO 30
<211> LENGTH: 70
<212> TYPE: DNA
<213> ORGANISM: Artificial sequence
<220> FEATURE:
<223> OTHER INFORMATION: Linear Circularising Probe 7

<400> SEQUENCE: 30
tttgtggaga caggtatgtt aagtgaccgg cagcagattt gattagattt ggtaaaatat       60
gtggtcacac                                                              70

<210> SEQ ID NO 31
<211> LENGTH: 70
<212> TYPE: DNA
<213> ORGANISM: Artificial sequence
<220> FEATURE:
<223> OTHER INFORMATION: Linear Circularising Probe 8

<400> SEQUENCE: 31
tttgtggaga caggtatgtt aagtgaccgg cagcaagtaa tgtgatttga taaagaatat       60
gtggtcacat                                                              70

<210> SEQ ID NO 32
<211> LENGTH: 15
<212> TYPE: DNA
```

```
<213> ORGANISM: Artificial sequence
<220> FEATURE:
<223> OTHER INFORMATION: 5prime Target Recognition Sequence

<400> SEQUENCE: 32
ttgaactctg cttaa                                                      15

<210> SEQ ID NO 33
<211> LENGTH: 20
<212> TYPE: DNA
<213> ORGANISM: Artificial sequence
<220> FEATURE:
<223> OTHER INFORMATION: Microarray Address Sequence

<400> SEQUENCE: 33
gtaaagtaga ttatgttaga                                                 20

<210> SEQ ID NO 34
<211> LENGTH: 15
<212> TYPE: DNA
<213> ORGANISM: Artificial sequence
<220> FEATURE:
<223> OTHER INFORMATION: 3prime Target Recognition Sequence

<400> SEQUENCE: 34
caaaccagta cttac                                                      15

<210> SEQ ID NO 35
<211> LENGTH: 15
<212> TYPE: DNA
<213> ORGANISM: Artificial sequence
<220> FEATURE:
<223> OTHER INFORMATION: 5prime Target Recognition Sequence

<400> SEQUENCE: 35
cttccagata acagc                                                      15

<210> SEQ ID NO 36
<211> LENGTH: 20
<212> TYPE: DNA
<213> ORGANISM: Artificial sequence
<220> FEATURE:
<223> OTHER INFORMATION: Microarray Address Sequence

<400> SEQUENCE: 36
tgattttgat gtgtaagatt                                                 20

<210> SEQ ID NO 37
<211> LENGTH: 15
<212> TYPE: DNA
<213> ORGANISM: Artificial sequence
<220> FEATURE:
<223> OTHER INFORMATION: 3prime Target Recognition Sequence

<400> SEQUENCE: 37
gccgctgaag ggctt                                                      15

<210> SEQ ID NO 38
<211> LENGTH: 20
<212> TYPE: DNA
<213> ORGANISM: Artificial sequence
<220> FEATURE:
<223> OTHER INFORMATION: Microarray Address Sequence

<400> SEQUENCE: 38
tagagtaaat gaaaagtgat                                                 20
```

```
<210> SEQ ID NO 39
<211> LENGTH: 20
<212> TYPE: DNA
<213> ORGANISM: Artificial sequence
<220> FEATURE:
<223> OTHER INFORMATION: Probe Identification Sequence

<400> SEQUENCE: 39
tttgtagatt tgagtaagta                                                    20

<210> SEQ ID NO 40
<211> LENGTH: 90
<212> TYPE: DNA
<213> ORGANISM: Artificial sequence
<220> FEATURE:
<223> OTHER INFORMATION: Linear Circularising Probe 9

<400> SEQUENCE: 40
ttgaactctg cttaaatgtt aagtgaccgg cagcagtaaa gtagattatg ttagagattt        60
gattagattt ggtaacaaac cagtacttac                                         90

<210> SEQ ID NO 41
<211> LENGTH: 90
<212> TYPE: DNA
<213> ORGANISM: Artificial sequence
<220> FEATURE:
<223> OTHER INFORMATION: Linear Circularising Probe 10

<400> SEQUENCE: 41
cttccagata acagcatgtt aagtgaccgg cagcatgatt ttgatgtgta agattagtaa        60
tgtgatttga taaaggccgc tgaagggctt                                         90

<210> SEQ ID NO 42
<211> LENGTH: 90
<212> TYPE: DNA
<213> ORGANISM: Artificial sequence
<220> FEATURE:
<223> OTHER INFORMATION: Linear Circularising Probe 11

<400> SEQUENCE: 42
ttgaactctg cttaaatgtt aagtgaccgg cagcatagag taaatgaaaa gtgattttgt        60
agatttgagt aagtagccgc tgaagggctt                                         90

<210> SEQ ID NO 43
<211> LENGTH: 20
<212> TYPE: DNA
<213> ORGANISM: Artificial sequence
<220> FEATURE:
<223> OTHER INFORMATION: Probe Detection Sequence 3

<400> SEQUENCE: 43
tttgtagatt tgagtaagta                                                    20
```

USE OF MASS LABELLED PROBES TO DETECT TARGET NUCLEIC ACIDS USING MASS SPECTROMETRY

This invention relates to useful probe molecules for characterising biomolecules of interest, particularly nucleic acids. Specifically this invention relates to oligonucleotide probes that are cleavably linked to tags designed for detection by mass spectrometry and tandem mass spectrometry. In addition, this invention relates to associated methods for employing mass labeled probes to detect target nucleic acids using mass spectrometry.

REFERENCE TO SEQUENCE LISTING

In accordance with 37 CFR §1.824, Applicant encloses herewith a copy of the Sequence Listing in computer readable form (CRF) on one compact disc, file name 52135.WO01.SeqList received from ME14.11.06.txt, created Nov. 20, 2006, file size 10.2 kilobytes, the contents thereof being incorporated by reference herein. The content of the sequence listing recorded in computer readable form is identical to the written sequence listing and, includes no new matter.

BACKGROUND OF THE INVENTION

Nucleic acids are typically detected by contacting them with labelled probe molecules under controlled conditions and detecting the labels to determine whether specific binding or hybridisation has taken place. Various methods of labeling probes are known in the art, including the use of radioactive atoms, fluorescent dyes, luminescent reagents, electron capture reagents and light absorbing dyes. Each of these labeling systems has features which make it suitable for certain applications and not others. For reasons of safety, interest in non-radioactive labeling systems lead to the widespread commercial development of fluorescent labeling schemes particularly for genetic analysis. Fluorescent labeling schemes permit the labeling of a relatively small number of molecules simultaneously, typically 4 labels can be used simultaneously and possibly up to eight. However the costs of the detection apparatus and the difficulties of analysing the resultant signals limit the number of labels that can be used simultaneously in a fluorescence detection scheme.

More recently there has been development in the area of mass spectrometry as a method of detecting labels that are cleavably attached to their associated probe molecules. Until recently, Mass Spectrometry has been used to detect analyte ions or their fragment ions directly, however for many applications such as nucleic acid analysis, the structure of the analyte can be determined from indirect labeling. This is advantageous particularly with respect to the use of mass spectrometry because complex biomolecules such as DNA have complex mass spectra and are detected with relatively poor sensitivity. Indirect detection means that an associated label molecule can be used to identify the original analyte, where the label is designed for sensitive detection and a simple mass spectrum. Simple mass spectra mean that multiple labels can be used to analyse multiple analytes simultaneously. In fact, many more labels than can currently be used simultaneously in fluorescence based assays can be generated.

WO98/31830 describes arrays of nucleic acid probes covalently attached to cleavable labels that are detectable by mass spectrometry which identify the sequence of the covalently linked nucleic acid probe. The labeled probes of this application have the structure Nu-L-M where Nu is a nucleic acid covalently linked to L, a cleavable linker, covalently linked to M, a mass label. Preferred cleavable linkers in this application cleave within the ion source of the mass spectrometer. Preferred mass labels are substituted poly-aryl ethers. These application discloses a variety of ionisation methods and analysis by quadrupole mass analysers, TOF analysers and magnetic sector instruments as specific methods of analysing mass labels by mass spectrometry.

WO 95/04160 disclose ligands, and specifically nucleic acids, cleavably linked to mass tag molecules. Preferred cleavable linkers are photo-cleavable. These application discloses Matrix Assisted Laser Desorption Ionisation (MALDI) Time of Flight (TOF) mass spectrometry as a specific method of analysing mass labels by mass spectrometry.

WO 98/26095 discloses releasable non-volatile mass-label molecules. In preferred embodiments these labels comprise polymers, particularly biopolymers, and more particularly nucleic acids, which are cleavably attached to a reactive group or ligand, i.e. a probe. Preferred cleavable linkers appear to be chemically or enzymatically cleavable. This application discloses MALDI TOF mass spectrometry as a specific method of analysing mass labels by mass spectrometry.

WO 97/27327, WO 97/27325, WO 97/27331 disclose ligands, and specifically nucleic acids, cleavably linked to mass tag molecules. Preferred cleavable linkers appear to be chemically or photo-cleavable. These application discloses a variety of ionisation methods and analysis by quadrupole mass analysers, TOF analysers and magnetic sector instruments as specific methods of analysing mass labels by mass spectrometry.

WO 01/68664 and WO 03/025576 disclose organic molecule mass markers that are analysed by tandem mass spectrometry. These applications disclose mass markers comprised of two components, a mass tag component and a mass normalization component that are connected to each other by a collision cleavable group. Sets of tags can be synthesised where the sum of the masses of the two components produce markers with the same overall mass. The mass markers are typically analysed after cleavage from their analyte. Analysis takes place in an instrument capable of tandem mass spectrometric analysis. In the first stage of analysis, the MS/MS instrument is set to select ions with the mass-to-charge ratio that corresponds to the mass marker comprising both the mass tag and mass normaliser, which may be referred to as the 'parent ion'. This selection process effected by the MS/MS instrument allows the markers to be abstracted from the background. Collision of selected the marker ions in the second stage of the analysis separates the two components of the tag from each other. Only the mass tag fragments of the parent ion, which may be referred to as the 'daughter ions' are detected in the third stage of analysis. This allows confirmation that the ion selected in the first stage of analysis is from a mass marker and not from a contaminating ion, which happens to have the same mass-to-charge ratio as the parent ion. The whole process greatly enhances the signal to noise ratio of the analysis and improves sensitivity. This mass marker design also compresses the mass range over which an array of mass markers is spread as mass markers can have the same mass as long as they give rise to mass tag fragments that are uniquely resolvable. Moreover, with isotopes, this mass marker design allows the synthesis of markers, which are chemically identical, have the same mass but which are still resolvable by mass spectrometry. Use of these markers to identify oligonucleotide probes is described.

Thus, the prior art provides oligonucleotide probes cleavably linked to tags that are detectable by mass spectrometry.

The prior art also shows that these probes enable multiplexing of nucleic acid probe binding assays. However, multiplexed assays require more than just multiple tags. Many nucleic acid probe binding assays do not function well when multiplexed because of problems of cross-hybridisation. This is a particular problem for polymerase chain reaction (PCR) based assays, for which it is very costly and time-consuming to optimize reactions involving multiple primer pairs. The problems are due to the high risk of cross hybridization of primers to incorrect templates leading to cross-amplification of templates and hence to incorrect results.

However, some nucleic acid probe binding assay methods that enable high-order multiplexing are known in the art. Most notably, Oligonucleotide Ligation Assays (OLA) such as those described in U.S. Pat. No. 4,988,617, which discloses an assay for determining the sequence of a region of a target nucleic acid, which has a known possible mutation in at least one nucleotide position in the sequence. In this sort of assay, two oligonucleotide probes that are complementary to immediately adjacent segments of a target DNA or RNA molecule which, contains the possible mutation(s) near the segment joint, are hybridised to the target DNA. A ligase is then added to the juxtaposed hybridised probes. Assay conditions are selected such that when the target nucleotide is correctly base paired, the probes will be covalently joined by the ligase, and if not correctly base paired due to a mismatching nucleotide(s) near the segment joint, the probes are incapable of being covalently joined by the ligase. The presence or absence of ligation is detected as an indication of the sequence of the target nucleotide.

Similar assays are disclosed in EP-A-185 494. In this method, however, the formation of a ligation product depends on the capability of two adjacent probes to hybridize under high stringency conditions rather than on the requirement of correct base-pairing in the joint region for the ligase to function properly as in the above U.S. Pat. No. 4,988,617. Other references relating to ligase-assisted detection are, e.g., EP-A-330 308, EP-A-324 616, EP-A-473 155, EP-A-336 731, U.S. Pat. No. 4,883,750 and U.S. Pat. No. 5,242,794.

Ligation mediated assays have a number of advantages over conventional hybridization based assays. The reaction is more specific than hybridization as it requires several independent events to take place to give rise to a signal. Ligation reactions rely on the spatial juxtaposition of two separate probe sequences on a target sequence, and this is unlikely to occur in the absence of the appropriate target molecule even under non-stringent reaction conditions. This means that standardised reaction conditions can be used enabling automation. In addition, due to the substrate requirements of ligases, incorrectly hybridised probes with terminal mismatches at the ligation junction are ligated with very poor efficiency. This means that allelic sequence variants can be distinguished with suitably designed probes. The ligation event creates a unique molecule, not previously present in the assay which enables a variety of useful signal generation systems to be employed to detect the event. This high specificity makes ligation based assays easier to multiplex as disclosed in provisional U.S. application 20030108913.

Further improvements in stringency and multiplexing can be achieved using circularising probes. Circularising probes comprise a single oligonucleotide probe, typically about 70 nucleotides in length or greater, in which the two probe sequences that are to be ligated to each other are located at either end of the probe molecule. The probe sequences are designed so that when they bind to their target sequence, the two probe sequences are brought into juxtaposition. The probe sequences can then be ligated to form a closed circular loop of DNA. Since both probe sequences are linked to each other, when one probe sequence binds to its target, binding of the second probe sequence takes place with rapid kinetics. This ensures that intra-molecular ligation is much more likely than inter-molecular ligation reducing cross-ligation of probes to very low levels. In addition, cross-ligated probes are still linear and it is highly unlikely that two or more probes will cross-ligate to form a circular species. Similarly, mismatched probes, i.e. probes that have bound to a target that does not exactly match the probe sequence, are unable to ligate and therefore will not be circularized. This all means that correctly reacted probes can be distinguished from incorrectly reacted probes by the fact that correctly reacted probes are circular. The ability to resolve correctly matched probes means that large numbers of probes can be used simultaneously in a single reaction. The key to using circularizing probes lies in being able to obtain a signal from circularised probes rather than from non-circularised probes and various methods have been disclosed in the prior art to date.

The first disclosure of circularizing probes appears to have been made by Aono Toshiya in JP 4262799 and JP 430-4900. These applications both disclose the use of ligation reactions with circularising probes.

Circularisation is detected by the ability of circularized probes to undergo linear Rolling Circle Amplification (RCA). The methodology disclosed in the above Japanese applications comprises contacting the sample in the presence of a ligase with a probe oligonucleotide. Correctly hybridised probes will be circularized by ligation and will act as a template in a RCA polymerization reaction. A primer, which is at least partially complementary to the circularised probe, together with a strand-displacing nucleic acid polymerase and nucleotide triphosphates are added to the circularized sequences and a single stranded nucleic acid is formed which has a tandemly repeated sequence complementary to the circularized probe and at least partially to the template. The amplification product is then detected either via a labelled nucleotide triphosphate incorporated in the amplification, or by an added labelled nucleic acid probe capable of hybridizing to the amplification product.

Other methods based on RCA of circularized probes have been disclosed in U.S. Pat. No. 5,854,033 and related divisions of this application published as U.S. Pat. No. 6,344,329, U.S. Pat. No. 6,210,884 and U.S. Pat. No. 6,183,960. The most notable difference between the disclosure of these applications and the disclosure of JP 4262799 and JP 430-4900, is the use of hyper-branching RCA. In this method, a second primer that is at least partially complementary to the single-stranded product of linear RCA of a circularized probe is added to the reaction. This results in a further geometric amplification of the single stranded product.

Another method for resolving circularized probes from non-circularised probes is disclosed in WO 95/22623. The methods disclosed in this application exploit the fact that circularized probes are not susceptible to degradation by exonucleases while unreacted linear probes are susceptible to degradation. In addition, cyclisation of a probe 'locks', the probe onto its target, i.e. the probes are resistant to being separated from their target. This allows circularized probes to be distinguished from linear probes by subjecting the probes to non-hybridising conditions. This approach to the use of circularizing probes is sometimes referred to as Padlock Probe technology.

Despite the ability of mass tags to enable multiplexing of nucleic acid assays, none of the prior art on mass tags provides methods of analysing nucleic acids using circularising probes. Similarly, none of the prior art on circularising probes provides methods of detecting circularising probes suggests using mass spectrometry. It is thus an object of this invention to provide methods and reagents to exploit the abilities of both mass tags and circularising probes to be used in highly multiplexed nucleic acid detection assays.

BRIEF SUMMARY OF THE INVENTION

In a first aspect the invention provides a method of detecting a target nucleic acid comprising a) contacting the sample, under hybridizing conditions, with a probe for said target nucleic acid, wherein said probe comprises two terminal nucleic acid target recognition sequences that are complementary to and capable of hybridizing to two neighbouring regions of the target sequence, and wherein the probe is linked to a tag that is identifiable by mass spectrometry;

b) covalently connecting the ends of the hybridized probe with each other to form a circularized-probe, which interlocks with the target strand through catenation;

c) cleaving the mass tag from the circularized probe; and d) detecting the mass tag by mass spectrometry.

In a second aspect, the invention comprises a method of detecting the presence of a target nucleic acid in a sample, which method comprises a) contacting the sample, under hybridizing conditions, with a probe for said target nucleic acid, wherein said probe comprises two terminal nucleic acid target recognition sequences that are complementary to and capable of hybridizing to two neighbouring regions of the target sequence, and wherein the probe comprises a probe identification sequence;

b) covalently connecting the ends of the hybridized probe with each other to form a circularized-probe, which interlocks with the target strand through catenation;

c) hybridizing a probe detection oligonucleotide to the probe identification sequence present in the said probe, where the probe detection oligonucleotide is cleavably linked to a mass tag;

d) cleaving the mass tag from the probe detection oligonucleotide; and e) detecting the mass tag by mass spectrometry.

In a third aspect, the invention provides a method of detecting the presence of a target nucleic acid in a sample, which method comprises a) contacting the sample, under hybridizing conditions, with a probe for said target nucleic acid, wherein said probe comprises two terminal nucleic acid target recognition sequences that are complementary to and capable of hybridizing to two neighbouring regions of the target sequence, and wherein the probe further comprises a probe identification sequence and a pair of primer binding sequences;

b) covalently connecting the ends of the hybridized probe with each other to form a circularized-probe, which interlocks with the target strand through catenation;

c) cleaving the circularized probe such that the opened probe has the primer binding sequences oriented to enable polymerase chain reaction amplification of the probe identification sequence;

d) hybridizing a probe detection oligonucleotide to the probe identification sequence present in the said probe, where the probe detection oligonucleotide is cleavably linked to a mass tag;

e) performing a primer extension reaction by providing a primer capable of hybridizing to the primer binding sequence upstream of the probe identification sequence and extending said primer with a polymerase having 5' exonuclease activity, so as to cleave the mass tag from the probe detection oligonucleotide; and f) detecting the mass tag by mass spectrometry.

In a fourth aspect, the invention provides a method of detecting the presence of a target nucleic acid in a sample, which method comprises a) contacting the sample, under hybridizing conditions, with a probe for said target nucleic acid, wherein said probe comprises two terminal nucleic acid target recognition sequences that are complementary to and capable of hybridizing to two neighbouring regions of the target sequence, and wherein the probe further comprises a probe identification sequence and a pair of primer binding sequences;

b) covalently connecting the ends of the hybridized probe with each other to form a circularized-probe, which interlocks with the target strand through catenation;

c) contacting one primer binding sequence with a complementary primer under conditions for rolling circle replication to occur, to provide a linear extension product;

d) contacting the linear extension product with a primer having the sequence of the second primer binding sequence, under conditions to provide for hyper-branching rolling circle replication;

e) hybridizing a probe detection oligonucleotide to the probe identification sequence present in the said probe, where the probe detection oligonucleotide is cleavably linked to a mass tag; and f) detecting the mass tag by mass spectrometry.

The first aspect of the invention set out above relates to a method for detection of a nucleic acid using a circularising probe in which a mass tag is present in the probe. The other aspects of the invention set out above in contrast use a probe detection sequence in the circularising probe, wherein the probe detection sequence is detected with a probe attached to a mass tag.

DETAILED DESCRIPTION OF THE INVENTION

Figure 1:
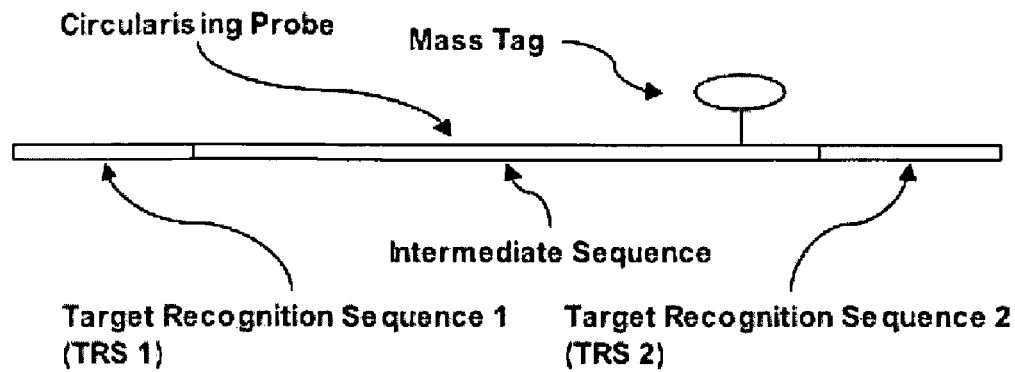
FIG. 1 illustrates a directly labelled Circularising Probe according to the first aspect of this invention. The probe comprises two Target Recognition Sequences (TRS1 and TRS2; marked as the grey regions) at either end of the probe. The intermediate sequence is shown in white. A mass tag is shown linked to the probe sequence. In some embodiments, more than 1 mass tag may be linked to a probe of the invention.

This invention describes reagents, methods and kits that exploit circularising probes to characterise nucleic acids by mass spectrometry.

DEFINITIONS

The term 'MS/MS' in the context of mass spectrometers refers to mass spectrometers capable of selecting ions, subjecting selected ions to Collision Induced Dissociation (CID) and subjecting the fragment ions to further analysis.

The term 'serial instrument' refers to mass spectrometers capable of MS/MS in which mass analysers are organised in series and each step of the MS/MS process is performed one after the other in linked mass analysers. Typical serial instruments include triple quadrupole mass spectrometers, tandem sector instruments and quadrupole time of flight mass spectrometers.

A Linear Circularising Probe (LCP) is probe sequence where the two termini of the probe comprise Target Recognition Sequences (TRS) that are designed to hybridise in juxtaposition on a target nucleic acid. The 3' terminus of the probe preferably comprises a free hydroxyl group while the 5' hydroxyl group is preferably phosphorylated. These probes are designed so that the TRS portions can be covalently linked to each other after correct hybridization to their target to form a circular molecule.

A Closed Circularizing Probe (CCP) is simply a name for an LCP whose TRS regions have been covalently linked to form a circular molecule.

A Probe Identification (PI) sequence is a sequence present in an LCP that allows the LCP to be identified through hybridisation with an appropriate Probe Detection Sequence that is preferably labelled with a unique mass tag.

A Probe Detection Sequence (PDS) is a labelled probe sequence that is at least partially complementary to a Probe Identification sequence and through hybridisation with a PI sequence it can be used to identify the presence of an LCP or CCP. Generally, the PDS probes are applied in a way that ensures that only CCPs are detected.

A Primer Binding Site (PBS) is a sequence that is present in an LCP or CCP that allows for the binding of a primer oligonucleotide so that the primer can facilitate replication of the CCP. Primers for rolling circle replication and for PCR can be used with this invention.

A primer for rolling circle replication is referred to as a Rolling Circle Primer (RCP) while a primer for PCR is simply referred to as a PCR primer.

Overview of the Invention

Circularising probes have a number of distinct advantages when compared to other approaches for SNP analysis and Gene Expression Profiling. The most widely used technologies at the moment that enables analysis of both SNPs and Gene Expression are microarrays and Real Time PCR. Both of these technologies have a number of disadvantages. Both these technologies typically require conversion of RNA into cDNA by reverse transcription prior to analysis. For mRNA analysis on microarrays, this typically requires the presence of a polyadenylation sequence at the 5' end of the mRNA to allow a generic amplification reaction. This means that RNA species that are not polyadenylated are difficult to analyse with microarray techniques, such as bacterial or viral RNA. For PCR based analysis of RNA, the lack of polyadenylation is not such a problem but PCR requires a pair of primers to be designed for each RNA species. Because each primer can potentially cross-hybridise and thus cross-amplify incorrect RNA molecules, PCR primer pairs must have a very high level of specificity. However, even with careful optimisation it is very difficult to design reactions with more than 20 pairs of specific PCR primers. Circularising probes have the advantage that large numbers can be used simultaneously in a single reaction (Hardenbol et al., Nature Biotechnology 21(6) pages 673-678, 2003) but can be designed for specific sequences, rather than relying on polyadenylation making Circularising probes ideal for analysis of bacterial and viral RNA. In addition, the ability to analyse numerous species simultaneously will allow analysis of viral RNA and bacterial simultaneously with human mRNA for example allowing expression changes in both host and infectious agent to be analysed simultaneously during studies of infection. The use of mass tags to detect circularisation events, as disclosed in this invention, has many advantages, since large arrays of isotopic tags can be generated. The use of isotopic tags means that accurate quantification is enabled as the relative abundances of isotope tags are an accurate indicator of the levels of the expression products.

In addition, the high specificity of circularising probes and the ability to accurately measure expression changes with isotopic mass tags allows both measurement of expression changes and the presence of genetic variation to be performed simultaneously. An example of an application of this ability would be viral load monitoring, where it is desirable to detect not only the total amount of virus, but the amount of each genetic variant. This is of importance in management of HIV treatment where specific genetic variations correspond to different forms of drug resistance. To be able to monitor this in a single test would enable much more effective management of this disease. Similar considerations apply to the treatment of cancers which also gradually evolve drug resistance.

Analysis of gene expression has a number of specific issues. Expression analysis typically involves the analysis of RNA species. RNA can be converted to cDNA by reverse transcription and numerous methods are known in the art (Wang J. et al., Biotechniques 34(2):394-400, "RNA amplification strategies for cDNA microarray experiments." 2003; Petalidis L. et al., Nucleic Acids Res. 31(22): e142, "Global amplification of mRNA by template-switching PCR: linearity and application to microarray analysis." 2003; Baugh L. R. et al., Nucleic Acids Res. 29(5):E29, "Quantitative analysis of mRNA amplification by in vitro transcription." 2001). However, it has been shown that target mediated ligation of LCPs can be performed with RNA targets directly, thus avoiding the need for conversion of RNA to cDNA (Nilsson M. et al., Nat. Biotechnol. 18(7):791-793, "Enhanced detection and distinction of RNA by enzymatic probe ligation." 2000). Thus in preferred embodiments of this invention involving RNA targets, it is preferred that LCPs are contacted directly with the target RNA molecules.

In preferred embodiments of the second aspect of the invention, correctly ligated CCPs are resolved from unreacted or incorrectly reacted LCPs by RCR. Target mediated ligation of LCPs to form CCPs interlocks the CCP with its target. It has been shown that RCR does still take place in this constrained environment but at a slightly lower efficiency than free circles (Kuhn H. et al., Nucleic Acids Res. 30(2):574-580, "Rolling-circle amplification under topological constraints." 2002) so where possible it is desirable to separate the CCPs from their target prior to RCR. When the target species is RNA it is possible to degrade the RNA component of an RNA/DNA duplex using RNAse H. Thus in embodiments of this invention where RCR is to be used, it may be preferred that prior to RCR, the CCP/RNA duplexes are degraded by contacting them with RNAse H.

Finally, in applications where many thousands of RNA species are analysed it is preferable that a large library of LCPs is applied in a single reaction and that a captured library of CCPs is generated from the RCR reaction as described above so that the library can be probed at leisure with multiple arrays of mass tagged Probe Detection Sequences.

Linear Circularising Probes:

A Linear Circularising Probe (LCP) of all aspects of the present invention comprise two Target Recognition Sequences (TRSs) which hybridise to two neighbouring regions of a target sequence. In the accompanying Figures, these are designated TRS1 and TRS2.

The size of each of TRS1 and TRS2 may vary and be independent of each other. Usually, one of the TRSs will be designed to detect an allelic sequence, e.g. a target sequence which may be one of two of more possibilities at a specific nucleotide. This may be designated TRS1, though it will be understood that this is an arbitrary designation and TRS1 may be at the 5' end or the 3' end of the LCP. The present invention may be used to determine which of two or more single nucleotide polymorphisms (SNPs) is present in a target sequence, by using a set comprising a mixture of two or more LCPs, each of which has a TRS1 specific for one SNP and a TRS2 which will usually be identical for each member of a set of LCPs.

The length of the TRS1 and position of the allelic nucleotide will be selected to allow the TRS1 which is completely homologous to its target to hybridise to that target sequence and be ligated to TRS2 whilst a TRS1 of the same set which differs by only a single residue does not hybridise sufficiently to undergo ligation with TRS2 when the target is that for the former TRS1.

Typically, the TRSs may be between 15 and 25 nucleotides in length each, though shorter lengths, e.g. of from 4 or more nucleotides, are not excluded. The precise size and composition of the TRSs may be selected by a person of skill in the art taking into account the specific nature of the target.

After TRS 1 and 2 have hybridized to the target molecule and any missing nucleotides between the LCP ends have been filled, the probe ends are connected to each other, typically by ligation with a ligase, to form a covalently Closed Circularizing Probe (CCP) molecule. Exemplary ligases are T4 DNA ligase, T7 DNA ligase, *E. coli* DNA ligase, and *Thermus thermophilus* DNA ligase. Alternative ways of effecting such covalent closure may, for example, be achieved by use of a catalytic RNA molecule or by chemical ligation.

By selecting the probe as well as the combined length of any gap filling nucleotides or oligonucleotides properly, the circular molecule formed will be wound around and will interlock with the target molecule. Typically, the circularized sequence should be 70 bases or greater for a probe comprised entirely of nucleotide linkages. Typically, for a nucleotide probe a size range of from 70 to 100 nucleotides may be used, e.g. a probe of about 80 or about 90 nucleotides in length.

A probe comprised of non-nucleotide linkages may have different steric limitations and in this way it may be possible to synthesise shorter oligonucleotide probes. It is sufficient, for the purposes of some aspects of the present invention, that only the actual TRS segments consist of nucleotides or optionally functionally analogous structures that can undergo ligation. The remainder of the LCP may have another chemical composition, comprising, for example, residues selected from peptides or proteins, carbohydrates or other natural or synthetic polymers. Such an intermediate structure of non-nucleotide nature may even be preferred with regard to stability and ease of introducing-labels or tags, and also since a non-nucleotide intermediate structure will not exhibit a secondary structure or cause mishybridization.

If, however, the probe structure does comprise only nucleic acid, the combined lengths of the component sequences of each LCP should preferably be such that the strands will leave the double helix on the same face 10 or a multiple of 10 bases apart, 10 bases representing approximately one turn of the DNA double helix.

Leaving a gap of one or more nucleotides between TRS 1 and TRS 2 may be advantageous as the gap filling step can improve specificity of the recognition reaction, but a gap is not critical and the method of the invention may be performed without it just as effectively, i.e. that TRS 1 and 2 are designed to in immediate juxtaposition on the target molecule, whereupon the two ends can be directly ligated to circularize the LCP to form a CCP.

Typically oligonucleotides for use as LCPs will be linear polymers of nucleotides and for many of the embodiments of this invention, this is preferred. It is however possible to introduce branched structures into nucleic acids, producing Y-shaped and comb-shaped branched structures (see for example Reese C. B. & Song Q., Nucleic Acids Res. 27(13): 2672-2681, "A new approach to the synthesis of branched and branched cyclic oligoribonucleotides." 1999; Horn T. et al., Nucleic Acids Res. 25(23):4835-4841, "An improved divergent synthesis of comb-type branched oligo-deoxyribonucleotides (bDNA) containing multiple secondary sequences." 1997; Braich R. S. & Damha M. J., Bioconjug Chem. 8(3): 370-377, "Regiospecific solid-phase synthesis of branched oligonucleotides. Effect of vicinal 2',5'- (or 2',3'-) and 3',5'-phosphodiester linkages on the formation of hairpin DNA." 1997; Horn T. & Urdea M S., Nucleic Acids Res. 17(17): 6959-6967, "Forks and combs and DNA: the synthesis of branched oligodeoxyribonucleotides." 1989).

Branched oligonucleotides are sometimes used to enable signal amplification without resorting to nucleic acid amplification, particularly comb-oligonucleotides in which a primary sequence specific linear oligonucleotide is linked to a series of secondary oligonucleotides (Horn T. et al., Nucleic Acids Res. 25(23):4842-4849, "Chemical synthesis and characterization of branched oligodeoxyribonucleotides (bDNA) for use as signal amplifiers in nucleic acid quantification assays." 1997). Thus in those aspects of the present invention in which the LCPs comprise a probe detection sequence, the LCPs may have a primary sequence which comprises the TRS sequences of the circularising probe and secondary oligonucleotides branched off the primary sequence, preferably all comprising an identical sequence, which act as the probe identification sequence. After circularisation of the primary sequence and removal of unreacted probes, the circularised sequence can be probed with mass tagged Probe Detection Sequences. Since the comb structure allows multiple Probe Identification sequences to be incorporated into a probe of this invention, this enables signal amplification without requiring amplification of the target sequence or the probe sequence.

The quantity of covalently circularized probe may be increased by repeating the cyclizing and dehybridizing steps one or more times. Thereby, multiple allele-specific LCPs will find and be ligated to form CCPs on target molecules. It is worth noting that when these reaction steps are repeated, it is possible that under appropriate conditions the same target sequence will mediate closure of multiple LCPs to form CCPs as the CCPs can become threaded on the target molecule. This is because the CCPs will move, or wander, to some extent along the target molecule during the dehybridizing step, making the target sequence available for a renewed hybridization by a non-circularized probe. If non-hybridising conditions are to be used to separate CCPs from unreacted and incorrectly ligated LCPs, and if multiple probe hybridization and closure cycles are to be used, it is, of course, necessary that the target molecule is reasonably large and that the target sequence is at a sufficient distance from the ends of the target molecule that the CCPs remain linked to the target molecule. For practical purposes, the target sequence should be at least about 200 base pairs from the nearest end depending on whether and how the target sequence is bound to a solid phase support. If the target sequence is free in solution, a longer distance may be required, especially in the case of long-lasting denaturing washes.

There are a number of advantages to gained by employing LCPs that can form covalently closed circular molecules upon correct hybridization to their target nucleic acids rather than detecting conventional labelled linear probes: First, each target requires only a single, synthetic probe molecule. Second, the ligation reaction provides high specificity of detection, since allelic sequence variants can be distinguished by the ligase. Third, the circularization of correctly hybridised probes provides a number of ways by which correctly matched probes can be distinguished from incorrectly matched probes: CCPs catenate with the target sequences, thereby becoming substantially insensitive to denaturants, the ends of the CCP become unavailable to exonuclease digestion and CCPs can mediate Rolling Circle Replication.

Finally, the simultaneous presence of two terminal probe sequences on one molecule confers kinetic advantages in the hybridization step.

Figure 2:
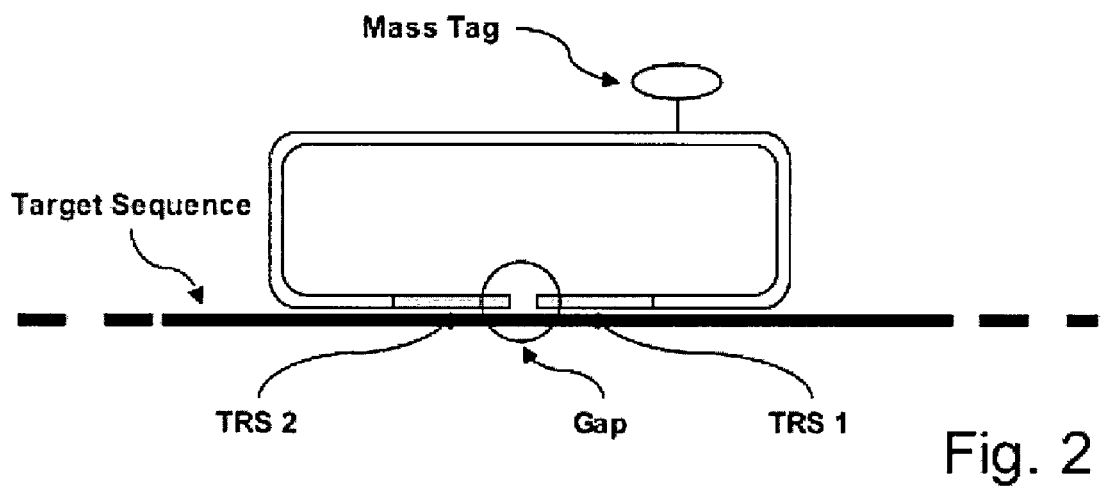
FIG. 2 illustrates hybridisation of a circularising probe to its target nucleic acid. It can be seen that the TRS regions are designed to hybridise in juxtaposition on the target, leaving a small gap, which may be just a missing phosphodiester linkage or a space of one or more nucleotides.
Figure 3:
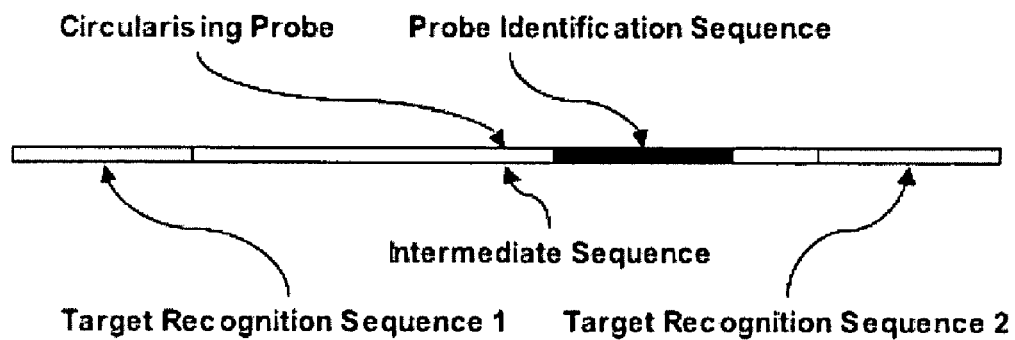
FIG. 3 illustrates a Circularising Probe according to the second aspect of this invention. The probe comprises two Target Recognition Sequences (TRS1 and TRS2; marked as the grey regions) at either end of the probe. The intermediate sequence is shown in white. A Probe Identification sequence (marked as the black region) is present in the Intermediate region (marked as the white region). The Probe Identification sequence is designed to uniquely identify the probe. In some embodiments, more than 1 Probe Identification sequence may be present in a probe of the invention.

Illustrated in FIG. 1 is a Linear Circularising Probe (LCP) according to the first aspect of this invention in which the probe is directly conjugated to a mass tag. The two termini of the probe comprise the Target Recognition Sequence (TRS) portion of the probe. The 3' terminus of the probe preferably comprises a free hydroxyl group while the 5' hydroxyl group is preferably phosphorylated. FIG. 2 illustrates the same directly labeled probe hybridized to a target nucleic acid sequence, such as a DNA strand, via two TRS end segments of the probe, designated TRS 1 and TRS 2. TRS 1 and TRS 2 are complementary to two respective almost contiguous sequences of the target molecule. A small gap is shown between the TRS segments. This gap may simply be a missing phosphodiester linkage or it may comprise a gap of 1 or more nucleotides. If the gap comprises a space of one or more nucleotides, it may be bridged by a second oligonucleotide probe or it may be filled by polymerase activity in the presence of the necessary nucleotide triphosphates.

If the target nucleic acid is sufficiently large, the CCP molecule will remain linked to the target molecule even under conditions that would release or degrade any hybridized non-cyclized LCPs. This is one way in which a circularization reaction produces a selectively detectable species, indicating the presence of the target molecule in a sample. Conditions that will denature or degrade a hybridized but non-cyclized probe include heat, alkali, guanidine hydrochloride, urea and other chemical denaturants or exonuclease activity, the latter degrading the free ends of any unreacted LCPs.

Gap-Filling:

As described above the TRS portions of an LCP can be designed to hybridize to a target sequence so that there is a small gap between the two TRS termini. This gap may be filled by extending the 3' TRS using a polymerase and 1 or more nucleotide triphosphates or, if the gap is sufficiently large it may be filled by one or more 'Gap Oligonucleotides'. The principles and procedures for gap-filling ligation are well known in the art as they are used in the method of 'gap LCR' (Wiedrnann et al., "PCR Methods and Applications" published by Cold Spring Harbor Laboratory Press, Cold Spring Harbor Laboratory, NY, pages S51-S64, 1994; Abravaya et al., Nucleic Acids Res., 23(4):675-682, 1995; European Patent Application EP0439182, 1991). In the "gap LCR" processes described in these publications, the gap-filling methods are applied to allow the ligation of two independent nucleic acid probes but these gap-filling are equally applicable to LCPs.

Hybridisation of LCPs with gaps, followed by gap-filling prior to ligation is advantageous as it provides higher stringency as multiple independent steps have to take place for correct closure of an LCP to form a CCP. Since these steps are unlikely to occur by chance, gap-filling offers a means for enhancing discrimination between closely related target sequences. Gap-filling should be performed with a different DNA polymerase from the polymerase used for rolling circle replication discussed later, and this polymerase will be referred to herein as a gap-filling DNA polymerase. Suitable gap-filling DNA polymerases are discussed in more detail later but in short when they extend the TRS from the 3' end of a hybridised LCP, they should not displace the hybridised TRS from the 5' end of the LCP. However, when the gap between the two TRS regions of an LCP is only a single nucleotide, then only the correct expected nucleotide needs to be added to allow extension of the 3' TRS to fill the gap. As long as the next base is not the same as the missing nucleotide, then most DNA polymerases can be used to fill the gap. This missing base is sometimes referred to as a "stop base". The use of "stop bases" in the gap-filling operation of LCR is described in European Patent Application EP0439182, for example. The principles of the design of gaps and the ends of flanking probes to be joined, as described in EP0439182, are generally applicable to the design of the gap spaces between the ends of the TRS portions of the LCPs of this inventions.

Figure 5A:
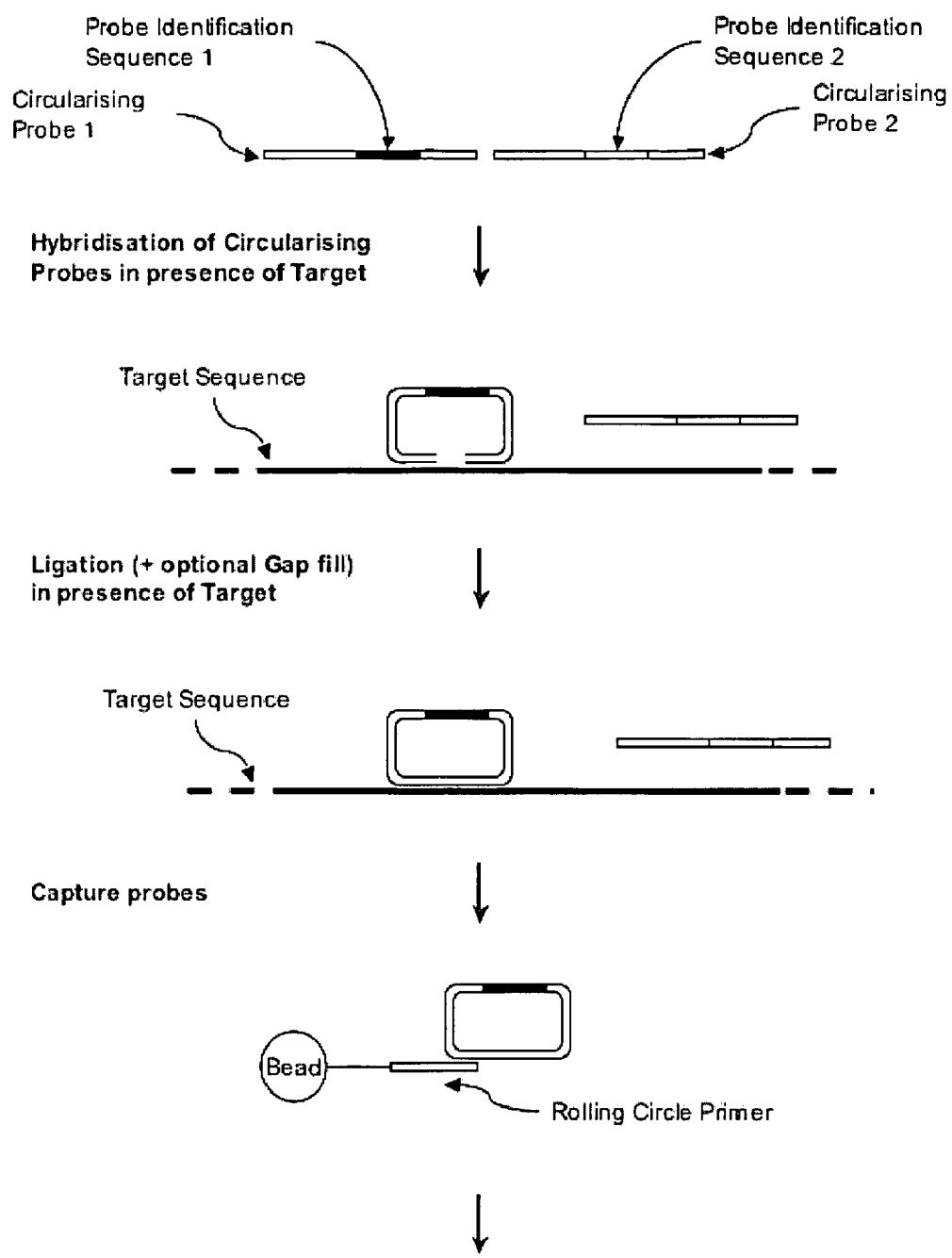
FIGS. 5a and 5b schematically illustrate the use of Circularising Probes that comprise Probe Identification Sequences in a method according to the second aspect of this invention. The details of the method are discussed in detail in the detailed description that follows.
Figure 5B:
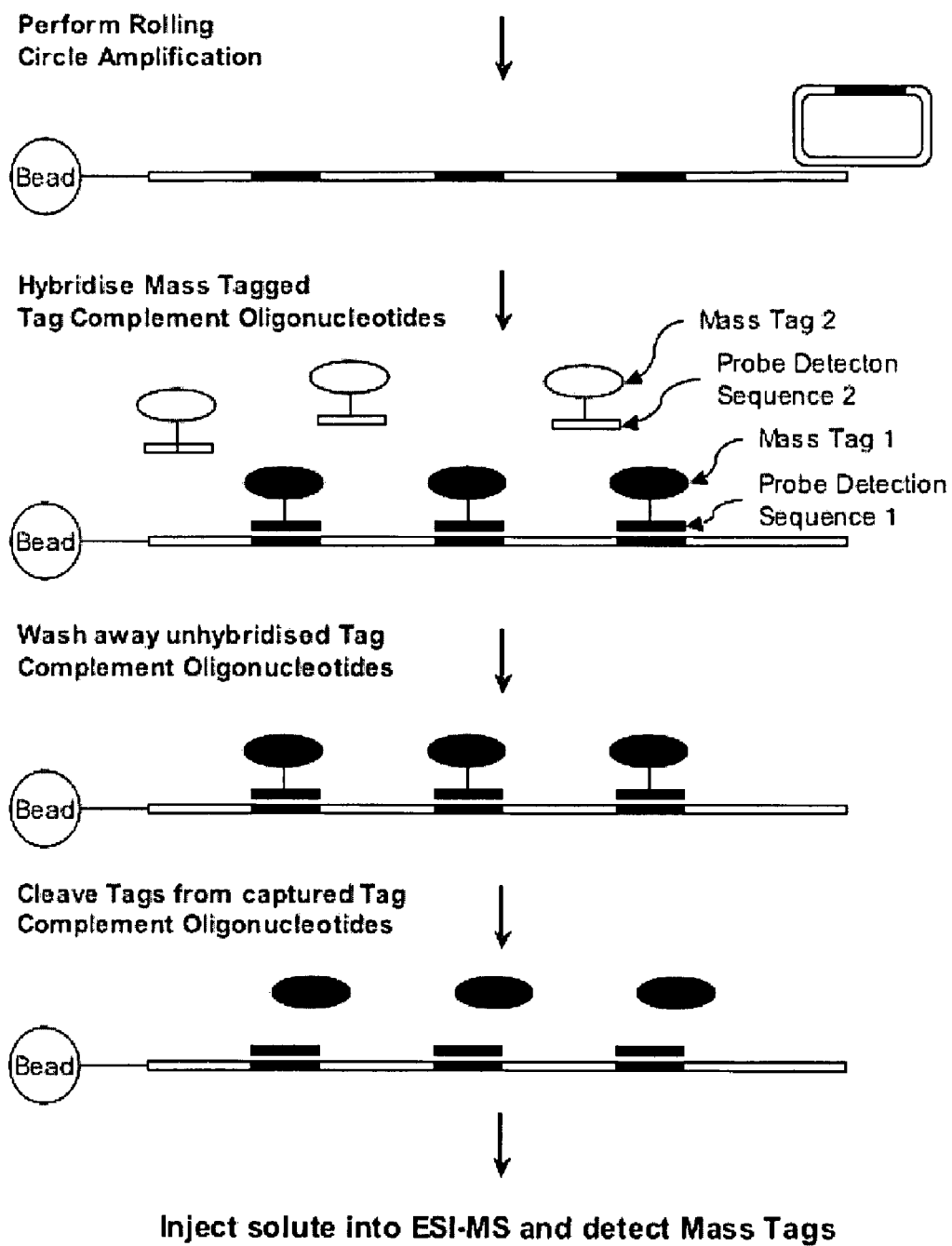

In embodiments of this invention which use rolling circle replication, it is possible for the gap-filling polymerase to interfere with rolling circle replication. To avoid this, the gap-filling DNA polymerase can be removed by extraction or inactivated with a neutralizing antibody prior to performing rolling circle replication. Such inactivation is analogous to the use of antibodies for blocking Taq DNA polymerase prior to PCR (Kellogg et al., Biotechniques 16(6): 1134-1137, 1994). More preferably, as shown in FIGS. 5a and 5b, after hybridization, gap-filling and ligation of LCPs to form CCPs, the CCPs (and any unreacted and incorrectly reacted LCPs) can be captured onto a solid phase support by a tethered oligonucleotide. The capture step can also be performed with a biotinylated oligonucleotide, which can be subsequently captured onto an avidinated solid support. The gap-filling polymerase can then be removed by washing the solid support and disposing of the liquid phase. Similarly, if the target sequence is captured onto a solid support, ligation of LCPs to form CCPs will leave the CCPs catenated with the target sequence and thus locked onto the solid support. This means that after ligation, both the gap-filling polymerase and unreacted LCPs can be washed away.

Figure 4A:
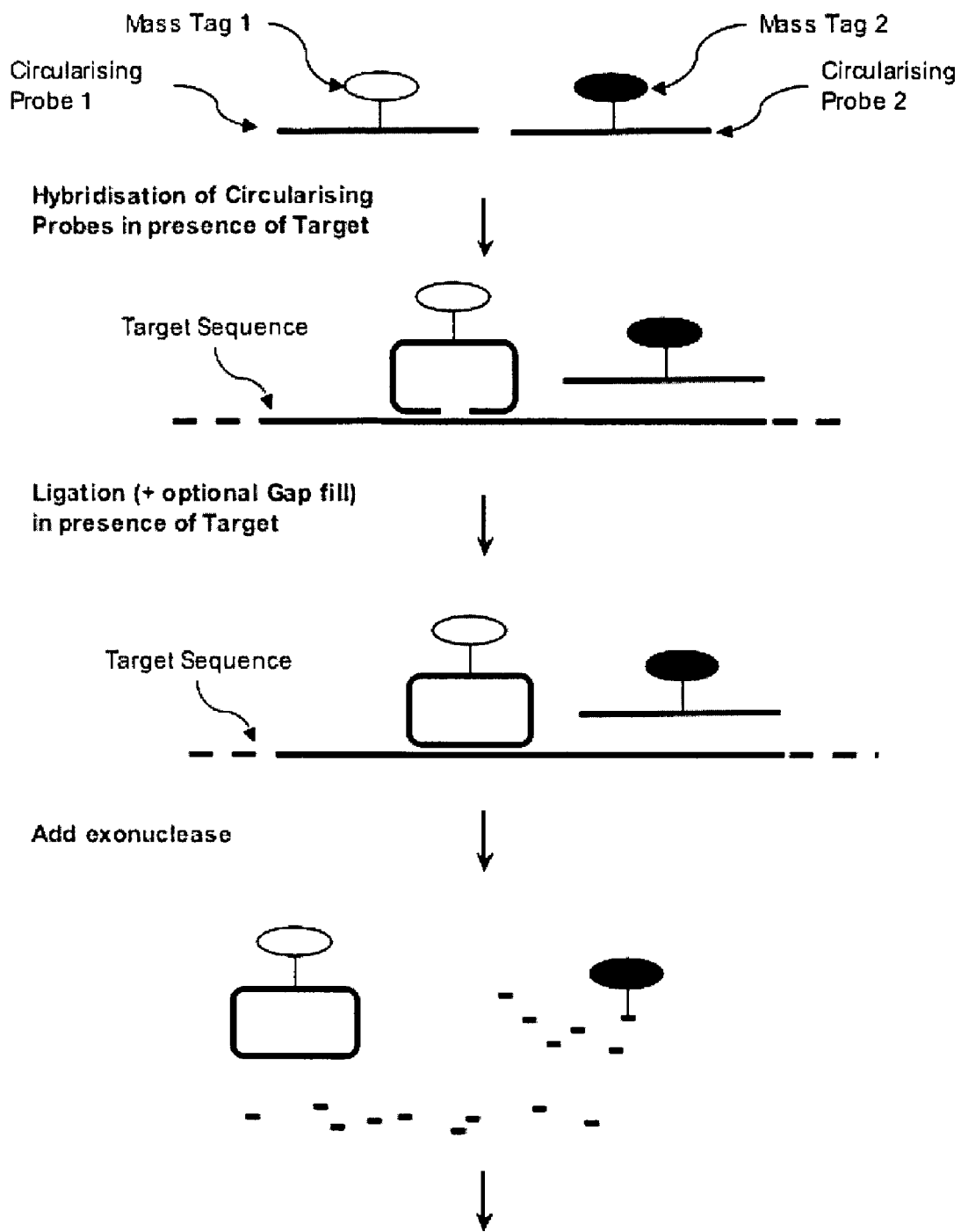
FIGS. 4a and 4b schematically illustrate the use of a directly labelled Circularising Probe in a method according to the first aspect of this invention. The details of the method are discussed in detail in the detailed description that follows.
Figure 4B:
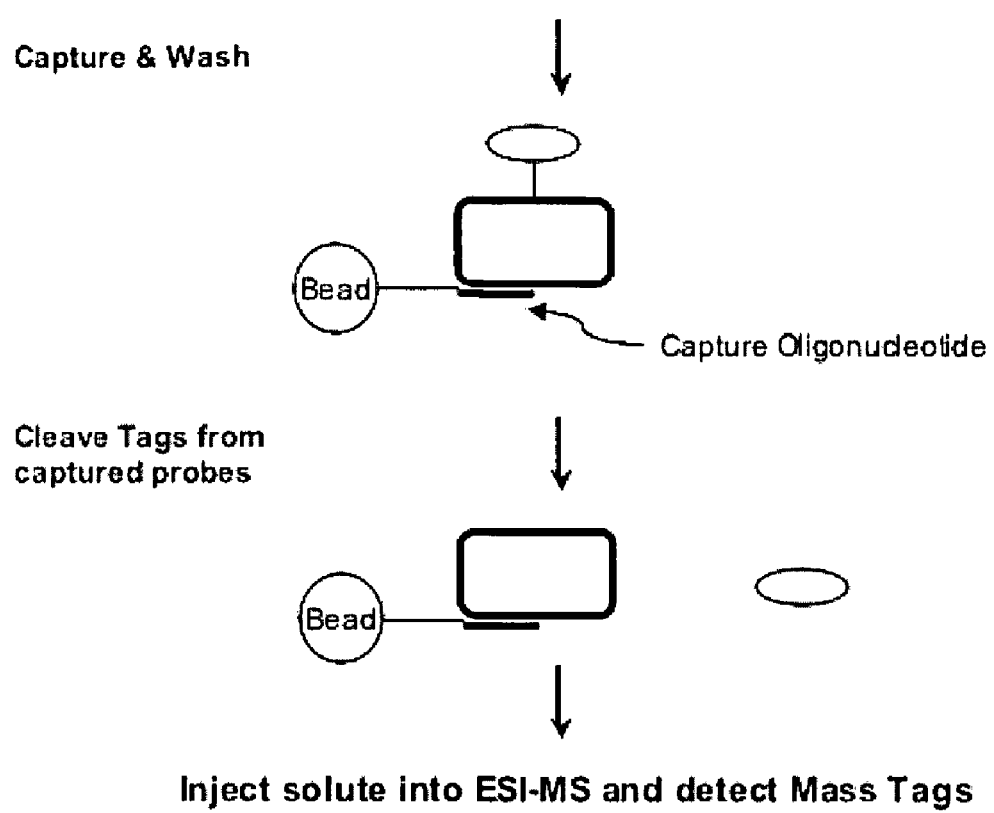

Directly Labelled Circularising Probes:

FIGS. 1, 2, 4a and 4b, schematically show an embodiment of this invention in which directly labelled probes are used. In FIGS. 4a and 4b a method for resolving correctly circularised probes from unreacted probes is shown. In these figures, the method is shown for two probes that recognise different alleles of a single target sequence. Each probe, designated Linear Circularising Probe 1 and Linear Circularising Probe 2, is covalently linked to and identified by a unique mass marker. After contacting LCP 1 and LCP 2 with the target sequence, only LCP 1 is capable of hybridising with the target to form a ligatable complex and so in the presence of ligase only LCP 1 is ligated to from a Closed Circularized Probe (CCP). The unreacted LCP 2 and any remaining LCP 1 can then be degraded by exonuclease activity while CCP 1 is protected by virtue of being circular. The gene 6 exonuclease of phage T7 provides a useful tool for the elimination of excess LCPs and any unreacted gap oligonucleotides. This exonuclease digests DNA starting from the 5'-end of a double-stranded structure. It has been used successfully for the generation of single-stranded DNA after PCR amplification (Holloway et al., Nucleic Acids Res. 21:3905-3906 (1993); Nikiforov et al., PCR Methods and Applications 3:285-291 (1994)). If a 'capture' sequence is incorporated into the LCP design, the surviving CCP 1 can be captured onto a solid phase support. The support can then be washed and in this way exonuclease digested LCP 2 and unreacted LCP 1, which cannot hybridise to the solid support, can be separated from the captured CCP 1. After washing away LCP 2 and its corresponding tags, the tags on CCP 1 can be cleaved from the CCP molecule. If the tags are linked via a trypsin cleavable linkage the tags can be easily cleaved by this enzyme. The solution phase containing the tags can then be injected into a mass spectrometer for detection of the tags.

Although only two tags have been shown in the shematic diagram in FIGS. 4a and 4b, many thousands of different LCPs can be used together as has been demonstrated previously (Hardenbol et al., Nature Biotechnology 21(6) pages 673-678, 2003).

In a further embodiment of this aspect of the invention, shown schematically in FIGS. 7a and 7b. Mass Tagged LCPs may be designed with a cleavable group in them. The cleavable group is positioned between the tag and the portion of the LCP that will allow it to be captured onto the solid support. In FIG. 7a, it can be seen that a capture sequence is present allowing the LCP to be captured by hybridisation to a tethered or biotinylated oligonucleotide. It would also be possible to directly biotinylate the LCPs. The presence of the cleavable group means that CCPs may be cleaved after their formation from LCPs. The cleavage step may take before or after the CCPs are capture onto a solid phase support. In FIG. 7b the cleavage is shown taking place before the capture step. The cleavage step ensures that the tagged portion of any unreacted LCPs is not retained on the solid support, as the tagged portion of the LCP is only linked to the capture sequence by the cleavable group. The ligation of LCPs to form CCPs means that the tag is linked through the ligated portion of the probe so that after the cleavage step the mass tags remain linked to the capture sequence (or biotinylated portion) of the probe. In this way, tags will only be captured for correctly closed CCPs allowing the tags from unreacted LCPs to be washed away as shown in FIG. 7b.

The cleavable group may be a type IIS restriction endonuclease recognition sequence, in which case the capture sequence may also serve as the cleavage site by providing the restriction sequence. In this situation, the tethered or biotinylated oligonucleotide is preferably hybridised with the LCPs and CCPs prior to cleavage to form a double stranded substrate for the restriction endonuclease. Alternatively, the cleavable group my be chemically cleavable. Replacement of one of the phosphodiester linkages in the backbone of an LCP with 3'-(N)-phosphoramidate or a 5'-(N)-phosphoramidate, results in a linkage that is more susceptible to acid hydrolysis than the rest of the probe. Alternatively, a uracil residue can be incorporated into the phosphodiester backbone. This residue is a substrate for the enzyme uracil deglycosylase, which depurinates this residue. The depurinated residue is then much more susceptible to hydrolysis than the rest of the probe molecule.

Indirect Detection of Circularising Probes:

In an alternative preferred embodiment of this invention, each different LCP of this invention comprises a unique Probe Identification (PI) sequence by which it can be identified through hybridisation with an appropriate Probe Detection Sequence that is labelled with a unique mass tag.

PI sequences are incorporated in the intermediate region of an LCP. Each PI sequence should uniquely identify its LCP. The PI Sequence is designed to allow detection by a corresponding mass tagged Probe Detection Sequence (PDS). The PI sequences, when amplified during Rolling Circle replication, result in tandemly repeated sequences that are complementary to the sequence of the mass tagged PDS probes. It may be desirable to have two or more PI sequences on an LCP as these will increase the signal from correctly hybridised mass-tagged PDS probes. There is no theoretical limit to the number of PI sequences that can be present in an LCP except the practicality of synthesizing and using very large LCPs comprising large numbers of PI sequences. When there are multiple PI sequences, they may have the same sequence or they may have different sequences, with each different sequence complementary to a different PDS probe. It is preferred that an LCP contain PI sequences that have the same sequence such that they are all complementary to a single PDS probe. The PI sequences can each be any length that supports specific and stable hybridization between the PI sequences and PDS probes. For practical purposes, a length of 10 to 35 nucleotides is preferred, with a length of 15 to 25, for example 15 to 20, nucleotides long being most preferred.

Similarly, the PDS sequences should have a length that is similar to the PI sequences.

In one embodiment, the Probe Detection Sequence may also be a branched oligonucleotide. For example, the PDS may comprise multiple sequences complementary to its Probe Identification sequence, in addition to comprising a mass tag. Such a PDS may be in the form of a Y-shaped oligonucleotide of a structure described by Suzuki Y. et al. (Nucleic Acids Symp Ser. 2000; (44):125-126, "Synthesis and properties of a new type DNA dendrimer.") comprising three copies of the PDS. A second Y-shaped branched oligonucleotide comprising three copies of the Probe Identification sequence when added to the tripartite PDS probe will assemble a dendrimer in which very large numbers of copies of the PDS, and consequently its associated mass tag will be present. If the tripartite PDS sequence is present in excess, then the dendrimer will have free PDS sequences available for hybridization to the Probe Identification sequences present in correctly circularized CCPs. In this way a very substantial signal amplification can be achieved without amplifying the target nucleic acid or CCPs.

FIGS. 5a and 5b illustrate an embodiment of the invention in which LCPs are identified after closure by the ability of CCPs to be selectively amplified by Rolling Circle Replication. In FIG. 5a, a schematic of a method of detecting DNA sequence variants is illustrated in which a pair of LCPs that identify different alleles of a DNA sequence are used. The LCPs in this assay are identifiable by their unique Probe Identification sequences. In FIG. 5a, a preferred embodiment of the invention is illustrated for a pair of probes that detect different variants of a single target molecule. In the first step, the pair of LCPs are contacted with their target sequence. Only one of the LCPs matches the target sequence correctly and hybridises to form a duplex, so that in the next step ligation only occurs at this correctly hybridised duplex converting the LCP into a CCP. This circular sequence is now a substrate for Rolling Circle Replication.

In some embodiments of this aspect of the invention, the unreacted LCPs can be degraded by exonuclease, but this is not shown in FIGS. 5a and 5b. In the next step, hybridisation of a captured primer with the CCP takes place to form a CCP/primer duplex. In the next step, polymerase extends the primer generating a tandem repeated sequence complementary to the CCP where the tandemly repeated complement is captured on a solid phase support. In alternative embodiments that primer sequence may be biotinylated rather than linked directly to a bead. In this sort of embodiment, the biotinylated product of the linear extension of the primer can then be captured onto an avidinated solid phase support after the extension reaction. The captured tandem repeat sequences also contain the complement of the Probe Identification (PI) sequences present in the LCP sequence. In the final steps of the assay shown in FIG. 5b, these complements of the PI sequences are probed with mass tagged Probe Detection Sequences. Since the targets of the PDS probes are captured on a solid phase support, the correctly hybridised PDS probes will be captured onto the support by the hybridisation reaction allowing unhybridised PDS probes to be washed away. After washing away unhybridised PDS probes, the mass tags on the correctly hybridised PDS probes can be cleaved off for subsequent detection by mass spectrometry.

Captured Libraries:

Although only two tags have been shown in the schematic diagram in FIGS. 5a and 5b, many different LCPs, such as several hundred or even more than a thousand can be used together as has been demonstrated previously (Hardenbol et al., Nature Biotechnology 21(6) pages 673-678, 2003). If many thousands of probes were used in the assay shown in FIGS. 5a and 5b, the result of the Rolling Circle Replication step in which the circularised probes sequences are copied onto beads will generate a 'captured library' of circularised probes that represents information in the probed sample. Captured Libraries have a number of advantages. After appropriate washing steps the library can be archived for future analysis. In addition, the library can be probed multiple times with the same mass tagged PDS probes to give signal amplification. In some embodiments of this aspect of the invention the captured library is probed in multiple sequential assays rather than in a single step using multiple distinct libraries of mass tagged PDS probes. In this way the same tags can be used to detect different Probe Identification sequences in the Captured Library. Thus, the use of Captured Libraries is an especially preferred embodiment of this invention. For the purposes of archiving Captured Libraries, it may be desirable to synthesise the captured libraries with exonuclease resistant nucleotide analogues that are compatible with polymerases such as boranophosphate nucleotides, or alpha-thio deoxynucleotide triphosphates.

Similarly, for long term storage, it may be preferable to generate captured libraries with covalently tethered oligonucleotides rather than with biotinylated oligonucleotides that are later captured onto avidinated beads to avoid the risk of sample loss by dissociation of the non-covalent biotin/avidin complex.

Rolling Circle Replication:

In preferred embodiments of the second aspect of the invention, rolling circle replication is applied to CCPs generated by target mediated ligation of LCPs. To effect Rolling Circle Replication (RCR) the circular single-stranded CCP DNA molecules are contacted with Rolling Circle Primers (RCPs) that hybridise to Primer Binding Sites in the CCPs. Extension of the RCPs by a strand displacing polymerase will result in tandem repeats of the complement of the CCP sequence as shown in FIGS. 5a and 5b. It can be seen from FIGS. 5a and 5b that in preferred embodiments the RCP is immobilized on a solid phase support or it is capable of being immobilized on a solid support after extension and Rolling Circle Replication of hybridised CCPs, by using a biotinylated RCP for example.

Specifically FIGS. 5a and 5b show a schematic of a method comprising the following steps:

(a) mixing one or more Linear Circularising Probes (LCP) with a target nucleic acid under conditions promoting hybridization, resulting in LCP-target duplexes, (b) contacting the LCP-target duplexes with a ligase, resulting in a ligation mixture, and incubating the ligation mixture under conditions promoting ligation of the LCPs to form CCPs, (c) contacting a rolling circle primer (RCP) under conditions that promote hybridization with the ligation mixture, resulting in a RCP-CCP duplex, (d) contacting the RCP-CCP duplex with a DNA polymerase under conditions promoting extension of the RCP to produce the complement of the CCP sequence, such that continuous extension of the RCP results in formation of tandem repeats of the complement of the CCP sequence.

Although FIGS. 5a and 5b show a schematic of an embodiment in which only 2 LCPs are present, thousands of LCPs may be present in a single reaction. Those LCPs that are ligated to form CCPs will be able to support RCA and thus will generate captured tandem repeats of their complement on a solid support. The solid support bound complement sequences for a number of different CCPs will be referred to as a Captured CCP Library.

In different embodiments of the second aspect of this invention, the Target Recognition Sequences may hybridize to the target nucleic acid sequence, with or without a central gap to be filled by one or more gap nucleotides or oligonucleotides.

For the purposes of Rolling Circle Replication (RCR) each LCP should comprise a Primer Binding Sequence (PBS). The PBS is complementary to the rolling circle primer (RCP). Each LCP should have at least one PBS, although if the LCPs are small, i.e. less than 100 nucleotides in length then preferably only a single PBS should be present. This allows rolling circle replication to initiate at a single site on CCPs. The primer complement portion and the corresponding rolling circle primer can have any desired sequence as long as they are complementary to each other. In general, the sequence of the PBS and the RCP should be chosen so that they are not significantly similar to any other portion of the LCP or any LCP in the library, when multiple LCPs are used together. The PBS can be any length that supports specific and stable hybridization between the PBS and the RCP. For this purpose, a length of 10 to 35 nucleotides is preferred, with a primer complement portion 16 to 20 nucleotides long being most preferred. The PBS can be located anywhere within the spacer region of an OCP. It is preferred that the PBS is adjacent to the 5' TRS, with the TRS and the PBS preferably separated by three to ten nucleotides, and most preferably separated by six nucleotides.

This location prevents the generation of any other spacer sequences, such as detection tags and secondary target sequences, from unligated LCPs during DNA replication.

A rolling circle primer (RCP) is an oligonucleotide having sequence complementary to the primer binding sequence of an LCP or CCP. This sequence is referred to as the complementary portion of the RCP. The complementary portion of a RCP and the cognate Primer Binding Sequence can have any desired sequence so long as they are complementary to each other. In general, the sequence of the RCP can be chosen such that it is not significantly complementary to any other portion of the LCP or CCP. The complementary portion of a rolling circle replication primer can be any length that supports specific and stable hybridization between the primer and the primer complement portion. Generally this is 10 to 35 nucleotides long, but is preferably 16 to 20 nucleotides long.

It is preferred that rolling circle replication primers also contain additional sequence at the 5' end of the RCP that is not complementary to any part of the LCP or CCP. This sequence is referred to as the Displacement region of the RCP. The Displacement region is located at the 5' end of the primer and serves to facilitate strand displacement during Rolling Circle Replication. The displacement region is typically a short sequence, preferably from 4 to 8 nucleotides long, and simply provides an unhybridised region of already displaced sequence that assists the strand displacing polymerase to start displacing the extended RCP.

In some embodiments of the Rolling Circle aspects of this invention, gene 6 exonuclease of phage T7 can be added after the ligation reaction, together with the DNA polymerase to be used to effect Rolling Circle Replication. To protect the Rolling Circle Replication product from degradation, the rolling circle primer can be composed of a few phosphorothioate linkages at the 5' end, to make the Rolling Circle Primer and its extension products resistant to the exonuclease (Nikiforov et al. (1994)). The exonuclease will degrade excess LCP molecules as they can become associated with the rolling circle DNA product and interfere with hybridization of PDS probes. The use of exonucloease digestion is a preferred method of eliminating unreacted LCPs and gap oligonucleotides.

Hyper-Branching Rolling Circle Replication:

Contacting a circular template with a single initiating primer and an appropriate polymerase results in linear Rolling Circle Replication and produces a linear tandemly repeated complementary copy of the circular template. If a second primer is present in the reaction, that is complementary to a site in the linear tandemly repeated copy of the circular template, this will bind to the tandemly repeated sequence at multiple locations and will initiate further replication. Since the second primer will bind at multiple locations, extension that initiates upstream of a primer will displace the extension product of that primer providing a linear single stranded template that allows further binding and extension of the initiating primer. This sort of reaction, therefore, gives rise to geometric amplification of the circular template and is sometimes referred to as hyper-branching RCR and will be referred to in this way in this application. This is a homogenous geometric amplification reaction and may be advantageous for use with this invention. For a fuller discussion on this sort of technique, see Zhang D. Y. et al. (Gene. 274(1-2):209-216, "Detection of rare DNA targets by isothermal ramification amplification." 2001) or Lizardi P. M. et al. (Nat. Genet. 19(3):225-32. "Mutation detection and single-molecule counting using isothermal rolling-circle amplification." 1998).

Accordingly, the use of a hyper-branching RCR reaction may be used in the present invention in order to provide a means of amplifying the probe identification sequence following ligation of a LCP.

Microarrays:

In further preferred embodiments of this invention, the LCP sequences comprise a Microarray Address Sequence in the intermediate region of the probe. A Microarray address sequence will have a sequence that is complementary to an oligonucleotide at a specific discrete location on a planar array.

In embodiments of the invention in which directly labeled LCPs are used, it is possible to hybridise CCPs that form as a result of template mediated ligation to a microarray. The Microarray Address Sequence will thus ensure that each CCP hybridizes to a discrete location on the microarray. In this way a combination of distinct Microarray Address Sequences and Mass tags can encode a very large number of LCPs that will then be uniquely identifiable by a unique combination of their Microarray Address Sequence and their Mass Tag. For example 1000 discrete Microarray Address Sequences, corresponding to 1000 discrete locations on a microarray, combined with 400 distinguishable Mass Tags, will allow 400 000 different LCPs to be uniquely identified in a single assay providing an unprecedented level of multiplexing in a single assay.

In alternative embodiments, in which LCPs are detected through a Probe Identification Sequence, which is distinct from the Microarray Address Sequence, the Microarray Address Sequence can be used to ensure that subsets of CCPs in a library of CCPs hybridise to distinct locations on the array. After hybridization, the correctly hybridised microarray probe sequence can be extended using an appropriate polymerase to effect rolling circle replication of the hybridised CCPs. Thus, the Microarray Address Sequence is also acting as the binding site for a Rolling Circle Primer, which happens to be immobilized at a discrete location on a planar array surface. In this way, a spatially resolved Captured Library of CCP sequences can be generated. The captured library can then be probed by hybridization with PDS sequences that recognize the Probe Identification sequence complements generated by the Rolling Circle replication that takes place at each array location.

After hybridization of directly labeled LCPs or after Rolling Circle Replication and hybridization of PDS sequences to the microarray, the microarray can then be treated with a MALDI matrix material such as 3-hydroxypicolinic acid or alpha-cyano-cinnamic acid. Having prepared the microarray in this way it can be loaded into a MALDI based mass spectrometer and the cleaved tags can be desorbed from discrete locations on the array by application of laser light to the desired location on the array.

In one aspect the invention thus provides a microarray comprising from 96 to 1000 discrete locations, such as from 96 to 500 discrete locations, each location comprising a discrete microarray address sequence complement. In another aspect, the invention provides a kit comprising such a microarray together with a set of circularising probes of the invention, wherein each member of the set of circularising probes comprises a discrete microarray address sequence which is capable of hybridizing to a microarray address sequence complement in the microarray.

In these microarray embodiments of the invention, appropriate methods for cleaving the tags from their associated probes on the array must be used. In one preferred approach, the tags are linked to their associated probes (linked either directly to LCPs or linked to PDS probes) through a photocleavable linker. This means that cleavage of the tags can take place at discrete locations on the array by exposure to light of the appropriate frequency. This light can be applied to the whole array prior to analysis by exposing the array to an intense light source. Alternatively, in a MALDI mass spectrometer, the laser used for desorption can be used to cleave the tags.

In an alternative embodiment, an acid cleavable linker can be used. Since most MALDI matrix materials are acidic, addition of the matrix will effect cleavage of the mass tags. In a further embodiment, the entire probe label complex can be desorbed, and cleavage of the tags can take place by collision using Post Source Decay in a Time-Of-Flight mass spectrometer or in the mass analyzer of an ion trap instrument or in a collision cell in alternative geometries that are used with MALDI, such as the Q-TOF geometry.

Practically speaking a microarray could comprise an array of wells on microtitre plates, for example, such that each well contains a single immobilised oligonucleotide that is a member of the array. In this situation a sample of the pooled reactions is added to each well and allowed to hybridise to the immobilised oligonucleotide present in the well. After a predetermined time the unhybridised DNA is washed away. The hybridised DNA can then be melted off the capture oligonucleotide. The released DNA can then be loaded into a capillary electrophoresis mass spectrometer or it can be injected into the ion source of a mass spectrometer.

Equally, and preferably, the array could be synthesised combinatorially on a glass 'chip' according to the methodology of Southern or that of Affymetrix, Santa Clara, Calif. (see for example: A. C. Pease et al. Proc. Natl. Acad. Sci. USA. 91, 5022-5026, 1994; U. Maskos and E. M. Southern, Nucleic Acids Research 21, 2269-2270, 1993; E. M. Southern et al, Nucleic Acids Research 22, 1368-1373, 1994) or using related ink-jet technologies such that discrete locations on the glass chip are derivitised with one member of the hybridisation array.

Polymerase Chain Reaction Amplification of CCPs:

In another preferred embodiment of this invention, correct closure of LCPs to form CCPs is detected by Polymerase Chain Reaction. In this embodiment the LCPs must comprise a pair of PCR Primer Binding Sequences (PPBS). The PPBS sites are preferably oriented so that the first primer must copy across the ligation junction that is formed when the LCP state of the probe is converted to the CCP by target mediated ligation. This means that the second PBS site does not become accessible to its primer unless the correct ligation event has taken place.

Figure 6A:
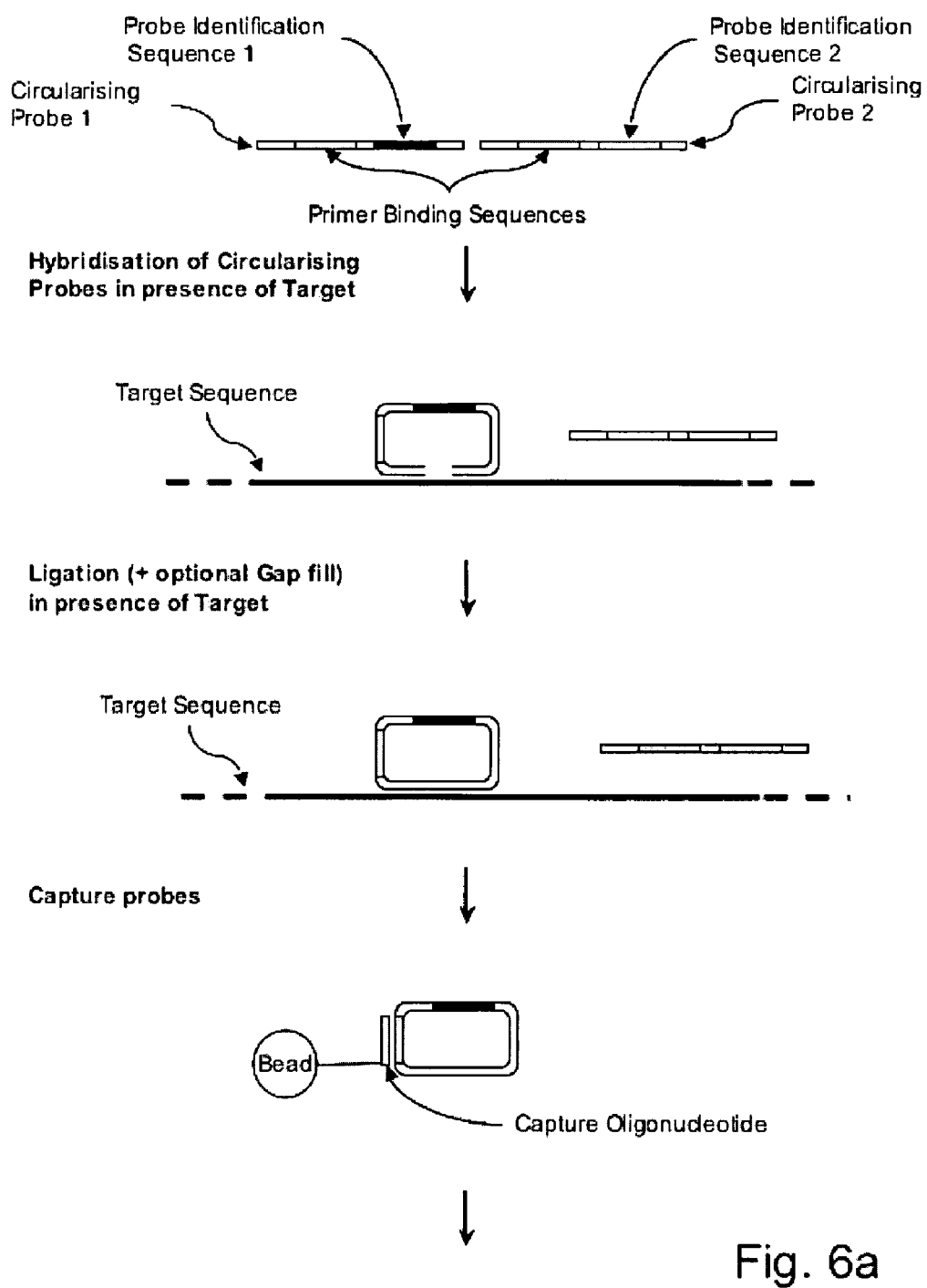
FIGS. 6a, 6b and 6c schematically illustrate the use of Circularising Probes that comprise Probe Identification Sequences and Primer Binding Sequences in a method according to the third aspect of this invention. The details of the method are discussed in detail in the detailed description that follows.
Figure 6B:
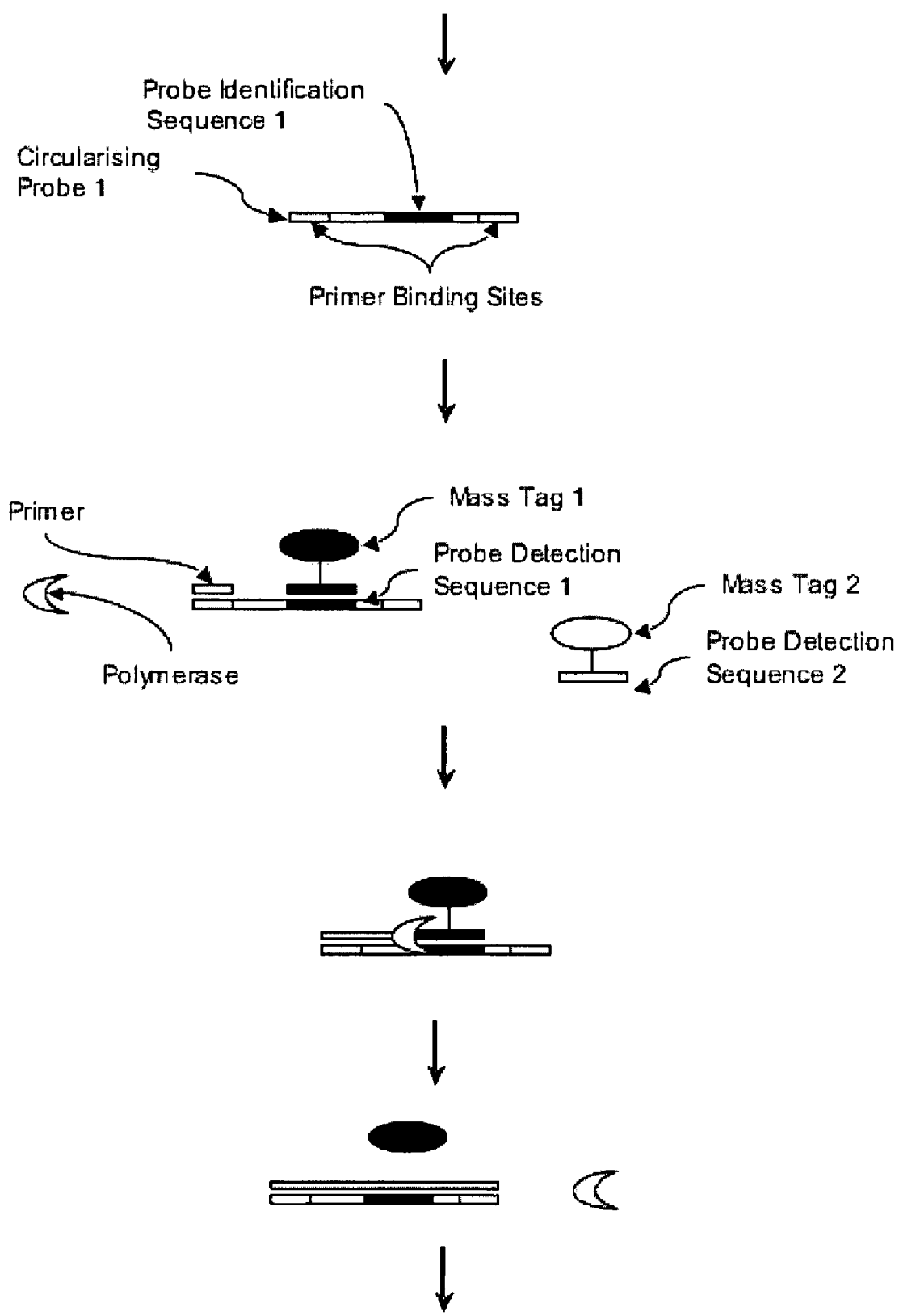
Figure 6C:
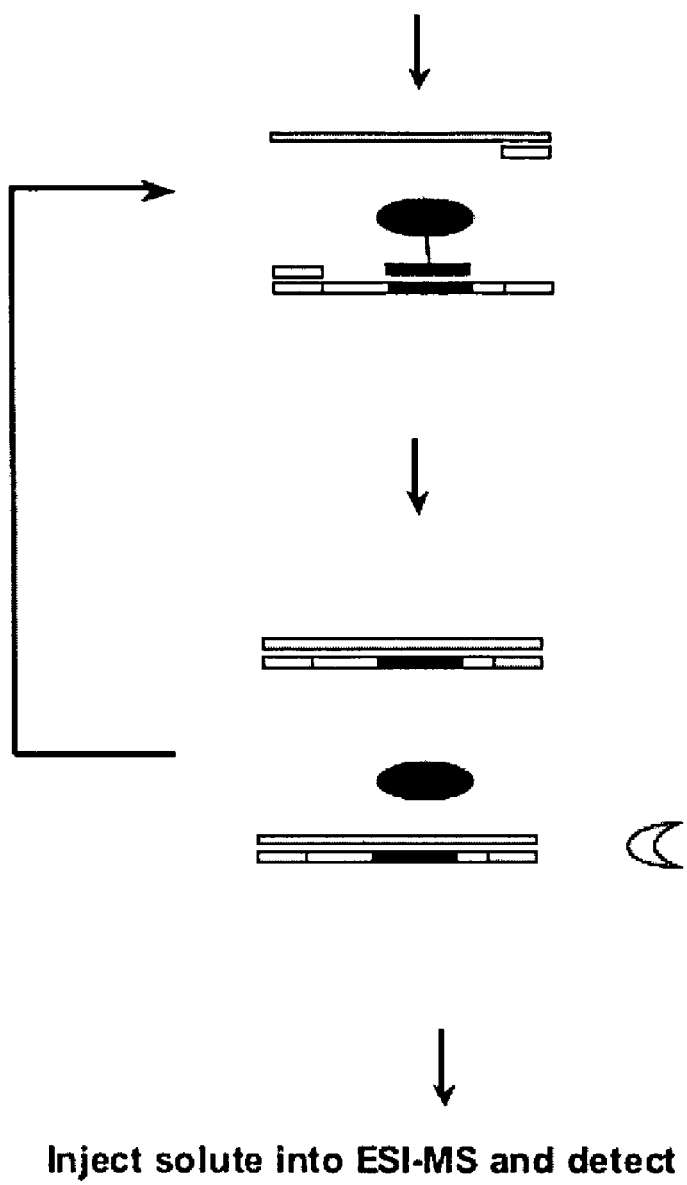

FIGS. 6a and 6b illustrate an embodiment of PCR based assay for the detection probe circularization using mass tags. These figures illustrate the assay for a pair of probes but in practice many thousands of probes could be used simultaneously. In the first stage of the assay the pair of LCPs are hybridised with their target. Ligation leads to closure of only one correctly hybridised probe. The probes are captured onto a solid phase support by an oligonucleotide that also comprises a restriction site for a type II restriction endonuclease. Cleavage of the captured probes by the endonuclease results in the formation of a linear structure in which parts of the LCP sequence have been rearranged. A similar process, using uracil deglycosylase to cleave the circularized probes, is described by Hardenbol et al. in Nature Biotechnology 21(6) pages 673-678, 2003 and is referred to as 'molecular inversion'. This results in the PPBS sites being in the correct orientation to enable exponential amplification of the CCPs only in the rearranged probes that have been correctly ligated by target mediated ligation. In FIG. 6b, the primer sequences are added along with Mass tagged Probe Identification Complement sequences. PCR is then effected with a thermostable polymerase with 5' to 3' exonuclease activity, which will release mass tags from correctly hybridised Probe Identification Complement sequences during the PCR reaction as shown in FIG. 6c. After the PCR reaction the released mass tags can be analysed by mass spectrometry.

Target Nucleic Acids:

Since the circularising probes, described in the present invention provide high specificity, it should be possible to detect the location of a unique sequence in total vertebrate DNA, particularly Human DNA. Other nucleic acid targets include bacterial DNA, viral DNA and/or RNA and expressed RNA from prokaryotes and eukaryotes.

In addition, the target nucleic acid library to be characterised by the methods and reagents of this invention may, for example, be DNA cloned in an M13 vector, or in a plasmid or phagemid vector that permits the excision of inserts as circular plasmids.

The target nucleic acid molecule, which may be DNA or RNA and which contains the specific sequence to be detected, should have a sufficient length to ensure that it can form a double helix, which is required for the circularized probe to interlock or catenate with the target molecule.

The target molecule may be a free molecule, but In some preferred embodiments of this invention, the target nucleic acids may be immobilized on a solid phase support.

Circularising probes can also be used for 'in situ' hybridization to tissue slices. With this sort of target, ligation of the LCPs to form CCPs will leave the probes firmly linked to their target sequences, thus allowing extensive washing to be performed. This washing will remove any circles that may have been formed by non-target-directed ligation, while circles ligated on-target are impossible to remove because they are topologically trapped (Nilsson et al. (1994)).

Reagents:

The methods of this invention require a variety of reagents, which are discussed in detail below.

Oligonucleotide Synthesis:

LCPs, gap oligonucleotides, rolling circle primers, PCR primers, mass tagged Probe Detection Sequences and any other oligonucleotides can be synthesized using standard oligonucleotide synthesis methods known in the art. Preferred methods are purely synthetic methods, for example, by the cyanoethyl phosphoramidite method (Beaucage and Caruthers, Tetrahedron Lett. 22: 1859-1862 (1981); McBride and Caruthers, Tetrahedron Lett. 24: 245-248 (1983)). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). PNA molecules can be made using known methods such as those described by Nielsen et al., Bioconjug. Chem. 5:3-7 (1994).

Since the circularizing probes of this invention are typically comprised of a series of distinct sequence components, such as a pair of TRS sequences separated by and intermediate sequence which is common to all probes, although it may comprise a unique probe identification sequence, it may be desirable to presynthesise these smaller subsequences and assemble them by ligation (Borodina et al., Anal Biochem.

318(2):309-313, "Ligation-based synthesis of oligonucleotides with block structure." 2003)

Methods for immobilization of oligonucleotides to solid-phase supports are well known in the art. For example, suitable attachment methods are described by Pease et al., Proc. Natl. Acad. Sci. USA 91(11):5022-5026, 1994 and Khrapko et al., Mol Biol (Mosk) (USSR) 25:718-730, 1991. A method for immobilization of 3'-amine oligonucleotides on casein-coated slides is described by Stimpson et al., Proc. Natl. Acad. Sci. USA 92:6379-6383 (1995).

Preferred methods of attaching oligonucleotides to solid-state substrates are described by Maskos, U. and Southern, E. M., Nucleic Acids Res 20(7): 1679-1684, "Oligonucleotide hybridizations on glass supports: a novel linker for oligonucleotide synthesis and hybridization properties of oligonucleotides synthesised in situ", 1992 and Guo et al., Nucleic Acids Res. 22:5456-5465 (1994).

For many applications of the oligonucleotides of this invention it is useful to know how stable they are, or more specifically at what temperature they will dissociate. The stability of DNA duplexes can be calculated using known methods for prediction of melting temperatures (Breslauer, K. J. et al., PNAS USA 83(11): 3746-3750, "Predicting DNA duplex stability from the base sequence.", 1986; Lesnick and Freier, Biochemistry 34:10807-10815, 1995; McGraw et al., Biotechniques 8:674-678, 1990; and Rychlik et al., Nucleic Acids Res. 18:6409-6412, 1990).

Mass Tagged Oligonucleotides:

A variety of mass tags can be applied with this invention although preferred mass tags are disclosed in WO 97/27327, WO 97/27325, WO 97/27331, WO 01/68664 and WO 03/025576. These applications all disclose tags that comprise polyamide compounds, essentially peptides or peptide-like tags, which means that these tags can be prepared using a number of peptide synthesis methods that are well known in the art (see for example Jones J. H., "The chemical synthesis of peptides", Oxford University Press (1991); Fields G. B. & Noble R. L., Int J Pept Protein Res 35(3): 161-214, "Solid phase peptide synthesis utilizing 9-fluorenylmethoxycarbonyl amino acids." (1990); Albericio F., Biopolymers 55(2): 123-139, "Orthogonal protecting groups for N(alpha)-amino and C-terminal carboxyl functions in solid-phase peptide synthesis." (2000)). In addition, the use of peptide and peptide-like tags enables coupling of these tags to oligonucleotides using a variety of peptide conjugation techniques that are known in the art.

A preferred mass tag is a tandem mass tag, comprising a mass marker moiety attached via a cleavable linker to a mass normalisation moiety, the mass marker moiety being fragmentation resistant. Such tandem mass tags are disclosed in WO01/68664 and WO 03/025576 (which refers to said tags as "mass labels"), the contents of which are incorporated herein by reference.

Where the present invention is used in the detection of multiple nucleotide sequences using multiple different mass tags, the tandem mass tags used may each be a member of a set of related mass tags. Overall, in such a set all of the mass tags in that set will be distinguishable from each other by mass spectrometry. This may be achieved by having the aggregate mass of each tag in the set to be same, but each mass marker moiety having a mass different from that of all other mass marker moieties in the set. Alternatively the mass marker moiety can be the same for each member of the set and the aggregate mass of each member is different from all other tags in that set.

The set of tags need not be limited to the two embodiments described above, and may for example comprise tags of both types, provided that all tags are distinguishable by mass spectrometry, as outlined above.

In one preferred aspect, each mass marker moiety in the set has a common basic structure and each mass normalisation moiety in the set has a common basic structure, and each mass tag in the set comprises one or more mass adjuster moieties, the mass adjuster moieties being attached to or situated within the basic structure of the mass marker moiety and/or the basic structure of the mass normalisation moiety. In this embodiment, every mass marker moiety in the set comprises a different number of mass adjuster moieties and every mass tag in the set has the same number of mass adjuster moieties.

By "common basic structure", it is meant that two or more moieties share a structure which has substantially the same structural skeleton, backbone or core. This skeleton or backbone may be for example comprise one or more amino acids. Preferably the skeleton comprises a number of amino acids linked by amide bonds. However, other units such as aryl ether units may also be present. The skeleton or backbone may comprise substituents pendent from it, or atomic or isotopic replacements within it, without changing the common basic structure.

Typically, a set of mass tags of the preferred type referred to above comprises mass tags which can be represented by the statement:

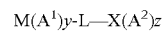

$$M(A^1)y\text{-}L\text{---}X(A^2)z$$

wherein M is the mass normalisation moiety, X is the mass marker moiety, $A^1$ and $A^2$ are mass adjuster moieties, L is the cleavable linker comprising the amide bond, y and z are integers of 0 or greater, and y+z is an integer of 1 or greater. Preferably M is a fragmentation resistant group, L is a linker that is susceptible to fragmentation on collision with another molecule or atom and X is preferably a pre-ionised, fragmentation resistant group. Preferably M and X have the same basic structure or core structure, this structure being modified by the mass adjuster moieties. The mass adjuster moieties ensure that the sum of the masses of M and X is the same for all mass tags in a set, but that each X has a distinct (unique) mass.

Mass adjuster moieties may be one or more isotopic substituents situated within the basic structure of the mass marker moiety and/or within the basic structure of the mass normalisation moiety and/or one or more substituent atoms or groups attached to the basic structure of the mass marker moiety and/or attached to the basic structure of the mass normalisation moiety. In a preferred aspect, the mass adjuster moieties $A^1$ and $A^2$ are independently selected from a halogen atom substituent, a methyl group substituent, a $^2$H isotopic substituent, a $^{13}$C isotopic substituent or a $^{15}$N isotopic substituent.

In preferred embodiments, the mass tags above are peptides where the mass normalisation moiety (M) and the mass marker moiety (X) are comprised of one or more amino acids, which may be natural amino acids or modified natural amino acids. In such embodiments, the mass adjuster moieties are isotopic substituents which are present as one or more atoms of the amino acids.

Preferably the cleavable linker (L) is preferably an amide bond between amino acids or may comprise one or more amino acids that facilitate cleavage by collision, such as proline (pro), aspartic acid (asp) or the dipeptide sequence asp-pro.

In a preferred embodiment, neutral amino acids are preferred as a mass normalisation moiety. These may be selected from the group consisting of alanine, glycine, leucine, phenylalanine, serine, threonine, tryptophan and valine. For the mass marker moiety charged amino acids may be used, since this facilitates ionisation and increases sensitivity. These may be selected from the group consisting of arginine, asparagine, aspartic acid, glutamic acid, glutamine, histidine, lysine and tyrosine.

Preferably a neutral amino acid of the mass normalisation moiety is used in combination with a charged amino acid of the mass marker moiety.

The mass normalisation and/or mass marker moieties which are amino acids may be varied in mass by the mass adjuster moieties as defined above.

Since the preferred compounds for use as mass tags are peptides, it is necessary to be able to produce peptide/oligonucleotide conjugates to provide the necessary reagents for this invention. Fortunately, numerous methods for the preparation of such conjugates are known in the art. There are two general approaches, complete synthesis of the conjugate for which a number of methods are known (Haralambidis J. et al., Nucleic Acids Res. 18(3):493-499, "The synthesis of polyamide-oligonucleotide conjugate molecules." 1990; de Koning M. C. et al. Curr Opin Chem. Biol. 7(6):734-740, "Synthetic developments towards PNA-peptide conjugates." 2003) or coupling of independently synthesized peptide or oligonucleotides to each other for which a variety of methods are known.

Methods for coupling tags including peptides to oligonucleotides via 5' amine functionalities are well known in the art (Smith L. M. et al., Nucleic Acids Res. 13(7):2399-2412, "The synthesis of oligonucleotides containing an aliphatic amino group at the 5' terminus: synthesis of fluorescent DNA primers for use in DNA sequence analysis." 1985; Sproat B. S. et al., Nucleic Acids Res. 15(15):6181-6196, "The synthesis of protected 5'-amino-2',5'-dideoxyribonucleoside-3'-O-phosphoramidites; applications of 5'-amino-oligodeoxyribonucleotides." 1987). In addition, it is possible to incorporate multiple amino groups into an oligonucleotide (Nelson P. S. et al, Nucleic Acids Res. 17(18):7179-7186, "A new and versatile reagent for incorporating multiple primary aliphatic amines into synthetic oligonucleotides." 1989) to allow multiple tags to be linked to the oligonucleotide. Methods for conjugating peptides to oligonucleotides via thiol groups at the termini of the oligonucleotides are disclosed in Arar et al., Bioconjug Chem. 6(5): 573-577, "Synthesis and antiviral activity of peptide-oligonucleotide conjugates prepared by using N alpha-(bromoacetyl)peptides.", 1995. Oligonucleotides can be coupled to peptides with terminal cysteine residues as disclosed in Wei et al., Bioconjug Chem. 5(5): 468-74, "Synthesis of oligoarginine-oligonucleotide conjugates and oligoarginine-bridged oligonucleotide pairs.", 1994.

To allow more than one tag to be incorporated per oligonucleotide, mass tags can be incorporated into the oligonucleotide through conjugation to thymidine analogues, for example, as disclosed in Brown et al., Tetrahedron Lett., 42: 2587-2592, "Synthesis of a Modified Thymidine Monomer for Site-Specific Incorporation of Reporter Groups into Oligonucleotides", 2001. In this publication, a thymidine analogue is described with a linker coupled to the purine ring of the thymidine. This thymidine analogue has a hydroxyl group protected with an FMOC group on the end of the linker that can be made available after the nucleotide has been coupled into an oligonucleotide during automated oligonucleotide syntheisis to allow a phosphoramidite modified tag to be incorporated into an oligonucleotide. Since this analogue can be incorporated within the chain, multiple linkers and hence tags can be coupled to the oligonucleotide.

DNA Ligases

Conversion of LCPs to CCPs is preferably carried out by a DNA ligase Preferred ligases are those that preferentially form phosphodiester bonds at nicks in double-stranded DNA. That is, ligases that are unable to ligate the free ends of single-stranded DNA at a significant rate are preferred. Thermostable ligases are especially preferred. Many suitable ligases are known, such as T4 DNA ligase (Davis et al., Advanced Bacterial Genetics—A Manual for Genetic Engineering (Cold Spring Harbor Laboratory, Cold Spring Harbor, N.Y., 1980)), E. coli DNA ligase (Panasnko et al., J. Biol. Chem. 253:4590-4592 (1978)). In preferred embodiments involving DNA targets, a thermostable DNA ligase is used to effect closure of LCPs to form CCPs as this will minimize the frequency of non-target-directed ligation events because ligation takes place at high temperature (50 to 75 degrees celsius). Examples of thermostable ligases include AMPLIGASE™ (Kalin et al., Mutat. Res., 283(2):119-123 (1992); Winn-Deen et al., Mol Cell Probes (England) 7(3):179-186 (1993)), the *T. aquaticus* DNA ligase (Barany, Proc. Natl. Acad. Sci. USA 88: 189-193 (1991), *Thermus scotoductus* DNA ligase, *Rhodothermus marinus* DNA ligase and *Thermus thermophilus* DNA ligase (Thorbjarnardottir et al., Gene 151:177-180 (1995); Housby J. N. et al., Nucleic Acids Res. 28(3): E10. (2000)).

The use of a thermostable ligase, enables a wide range of ligation temperatures to be used, allowing greater freedom in the selection of target sequences. A thermostable ligase also makes it easier to select ligation conditions that favor intramolecular ligation. Conditions are easily found where target mediated ligation of LCPs to form CCPs occurs much more frequently than tandem linear ligation of two LCPs. For example, circular ligation is favored when the temperature at which the ligation operation is performed is near the melting temperature ($T_m$) of the least stable of the left target probe portion and the right target probe portion when hybridized to the target sequence. When ligation is carried out near the $T_m$ of the target probe portion with the lowest $T_m$, the target probe portion is at association/dissociation equilibrium. At equilibrium, the probability of association in cis (that is, with the other target probe portion of the same LCP) is much higher than the probability of association in trans (that is, with a different LCP). When possible, it is preferred that the target probe portions be designed with melting temperatures near suitable temperatures for the ligation operation.

T4 DNA ligase is preferred for ligations involving RNA target sequences due to its ability to ligate DNA ends involved in DNA:RNA hybrids (Hsuih et al., Quantitative detection of HCV RNA using novel ligation-dependent polymerase chain reaction, American Association for the Study of Liver Diseases (Chicago, III., Nov. 3-7, 1995)).

DNA Polymerases

DNA polymerases useful in the rolling circle replication step of RCR must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ligated CCP. Any 5' to 3' exonuclease activity can result in the destruction of the synthesized strand.

It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases are bacteriophage Phi29 DNA polymerase (U.S. Pat. Nos. 5,198,543 and 5,001,050 to Blanco et al.), phage M2 DNA polymerase (Matsumoto et al., Gene 84:247 (1989)), phage PhiPRD1 DNA polymerase (Jung et al., Proc. Natl. Acad. Sci. USA 84:8287 (1987)), VENT™ DNA polymerase (Kong et al., J. Biol. Chem. 268:1965-1975 (1993)), Klenow fragment of DNA polymerase I (Jacobsen et al., Eur. J. Biochem. 45:623-627 (1974)), T5 DNA polymerase (Chatterjee et al., Gene 97:13-19 (1991)), PRD1 DNA polymerase (Zhu and Ito, Biochim. Biophys. Acta. 1219:267-276 (1994)), and T4 DNA polymerase holoenzyme (Kaboord and Benkovic, Curr. Biol. 5:149-157 (1995)).

A further preferred polymerase is the exonuclease(-) BST thermostable DNA polymerase available from New England Biolabs (Mass, USA). *Bacillus Stearothermophilus* is a thermophilic bacterium whose polymerase is highly processive and can be used at elevated temperature (65 degrees centigrade). A Klenow-like fragment without exonuclease activity is available (Phang S. M. et al., Gene. 163(1):65-68, "Cloning and complete sequence of the DNA polymerase-encoding gene (BstpolI) and characterisation of the Klenow-like fragment from *Bacillus stearothermophilus*." 1995; Aliotta J. M. et al., Genet Anal. 12(5-6):185-195, "Thermostable Bst DNA polymerase I lacks a 3→5' proofreading exonuclease activity." 1996) and it has been shown that this polymerase is highly effective for rolling circle replication (Zhang D. Y. et al., Gene. 274(1-2):209-216, "Detection of rare DNA targets by isothermal ramification amplification." 2001).

Of these Phi29 DNA polymerase and exo(-) BST DNA polymerase are most preferred.

Strand displacement can be facilitated through the use of a strand displacement factor, such as a helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in RCA include BMRF1 polymerase accessory subunit (Tsurumi et al., J. Virology 67(12):7648-7653 (1993)), adenovirus DNA-binding protein (Zijderveld and van der Vliet, J. Virology 68(2):1158-1164 (1994)), herpes simplex viral protein ICP8 (Boehmer and Lehman, J. Virology 67(2):711-715 (1993); Skaliter and Lehman, Proc. Natl. Acad. Sci. USA 91(22):10665-10669 (1994)), single-stranded DNA binding proteins (SSB; Rigler and Romano, J. Biol. Chem. 270:8910-8919 (1995)), and calf thymus helicase (Siegel et al., J. Biol. Chem. 267:13629-13635 (1992)).

The ability of a polymerase to carry out rolling circle replication can be determined by using the polymerase in a rolling circle replication assay such as those described in Fire and Xu, Proc. Natl. Acad. Sci. USA 92:4641-4645 (1995).

Another type of DNA polymerase can be used if a gap-filling synthesis step is used. When using a DNA polymerase to fill gaps, strand displacement by the DNA polymerase is undesirable. Such DNA polymerases are referred to herein as gap-filling DNA polymerases. Unless otherwise indicated, a DNA polymerase referred to herein without specifying it as a rolling circle DNA polymerase or a gap-filling DNA polymerase, is understood to be a rolling circle DNA polymerase and not a gap-filling DNA polymerase. Preferred gap-filling DNA polymerases are T7 DNA polymerase (Studier et al., Methods Enzymol. 185:60-89 (1990)), DEEPVENT™ DNA polymerase (New England Biolabs, Beverly, Mass.), and T4 DNA polymerase (Kunkel et al., Methods Enzymol. 154:367-382 (1987)). An especially preferred type of gap-filling DNA polymerase is the *Thermus flavus* DNA polymerase (MBR, Milwaukee, Wis.). The most preferred gap-filling DNA polymerase is the Stoffel fragment of Taq DNA polymerase (Lawyer et al., PCR Methods Appl. 2(4):275-287 (1993), King et al., J. Biol. Chem. 269(18):13061-13064 (1994)).

In embodiments of the third aspect of this invention, in which 5' exonuclease activity of the DNA polymerase is used to degrade mass tagged PDS probes during PCR amplification of CCPs, it is necessary to use a polymerase with the relevant 5' exonuclease activity. Taq polymerase is widely used for this purpose (Livak K. J., Genet Anal., 14(5-6): 143-9, "Allelic discrimination using fluorogenic probes and the 5' nuclease assay." (1999)) although a variety of polymerases have been assessed for this purpose and would be applicable with these embodiments of the invention (Kreuzer K. A. et al., Mol Cell Probes., 14(2): 57-60 (2000)).

RNA Polymerases

In some embodiments of this invention in which linear Rolling Circle Replication is used an RNA polymerase can be used to effect the replication reaction. An RNA polymerase which can carry out transcription in vitro and for which promoter sequences have been identified can be used in the disclosed rolling circle replication method. In this sort of embodiment, the Promoter sequences are used as the Primer Binding Sequences. A DNA primer is required in this sort of embodiment. The primer must be extended by a non-displacing polymerase, i.e. with the same characteristics as a gap-filling polymerase to produce a double stranded circular product with a nick. The nick may be ligated if desired. The RNA polymerase is then added to the promoter site and will initiate transcription if ribonucleotide triphosphates are present. Stable RNA polymerases without complex requirements are preferred. Most preferred are T7 RNA polymerase (Davanloo et al., Proc. Natl. Acad. Sci. USA 81:2035-2039 (1984)) and SP6 RNA polymerase (Butler and Chamberlin, J. Biol. Chem. 257:5772-5778 (1982)) which are highly specific for particular promoter sequences (Schenborn and Meirendorf, Nucleic Acids Research 13:6223-6236 (1985)). Other RNA polymerases with this characteristic are also preferred. Because promoter sequences are generally recognized by specific RNA polymerases, the OCP or ATC should contain a promoter sequence recognized by the RNA polymerase that is used. Numerous promoter sequences are known and any suitable RNA polymerase having an identified promoter sequence can be used. Promoter sequences for RNA polymerases can be identified using established techniques.

Kits:

The LCPs, Gap nucleotides or oligonucleotides, microarrays, Ligases, Polymerases, Primers and Mass Tagged Tag Complement Oligonucleotides described above can be packaged together in any suitable combination as a kit useful for performing the disclosed methods.

Analysis of Mass Tags by Mass Spectrometry:

The essential features of a mass spectrometer are as follows
Inlet System→Ion Source→Mass Analyser→Ion Detector→Data Capture System There are preferred inlet systems, ion sources and mass analysers and mass analysis methods for the purposes of analysing the mass tags and mass tagged probes of this invention and these are discussed in more detail below. Inlet systems may comprise separation systems that allow mass tags or mass tagged probes to be separated prior to mass spectrometry.

Cleavage of Mass Tagged Oligonucleotides:

The methods of this invention require that mass tags are cleaved from either directly labeled probes or from Probe Detection Sequences. Numerous methods are known in the art for the cleavage of probes from their corresponding tags.

See for example the disclosures of WO98/31830, WO 97/27327, WO 97/27325, WO 97/27331 and WO 98/26095. In preferred embodiments, enzymatic methods may be used. As discussed above, peptide and peptide-like tags are preferred tags for use with the methods of this invention. As such, specific endoproteases like trypsin are useful for cleaving tags which comprise specific amino acids, arginine or lysine in the case of trypsin. Thus a peptide tag comprising an arginine residue can be cleaved from its probe sequence by contacting the probe/tag conjugate with trypsin. Advantageously, arginine also gives rise to intense positive ions. Alternatively, chemical cleavage may be used to release tags. With peptide based tags, incorporation of a methionine residue between the tag peptide and the probe sequence allows the probe to be cleaved with cyanogen bromide under acidic conditions. As discussed above, in relation to microarrays, photocleavage is also a preferred method of cleaving tags from their associated probes, for which details can be obtained from the disclosure of WO 95/04160, which describes methods of synthesising probes and cleaving said probes. In another preferred embodiment of this invention cleavage may take place within the mass spectrometer by collision. The amino acid proline and aspartic acid undergo low energy collisions. This means that incorporation of a proline or aspartic acid residue or both together to form an asp-pro linkage between the tag peptide and the probe sequence allows the probe to be readily cleaved by low energy collision without substantial dissociation of the tag peptide. Collision cleavage must obviously take place after injection of the mass tagged probes or probe detection sequences into the mass spectrometer.

Separation of mass tagged oligonucleotides by chromatography or electrophoresis:

In further embodiments of the second aspect of this invention, libraries of PDS sequences can be generated in which the PDS comprises additional electrophoretic or chromatographic mobility modifying components. These mobility modifiers may comprise additional nucleotides or may comprise specifically designed mobility modifiers (Baron, H. et al., Nature Biotechnology 14: 1279-1282 (1996). The mobility modifiers ensure that PDS probes that recognise different Probe Identification sequences but which carry the same mass tag can be resolved by having different elution times in an electrophoretic or chromatographic separation. In this way a large array of PDS probes can be identified by a unique combination of their associated mass tag and the size of their mobility modifier. After hybridisation of these mobility modified PDS sequences with their corresponding probes, the probes are subjected to an electrophoretic or chromatographic separation prior to analysis by mass spectrometry. This is preferably Capillary Electrophoresis or High Performance Liquid Chromatography (HPLC), both of which can be coupled directly to a mass spectrometer for in-line analysis of the mass tagged oligonucleotides as they elute from the separation column. A variety of separation techniques may be performed by HPLC but reverse phase chromatography is the most widely used method for the separation of oligonucleotides prior to mass spectrometry.

In these embodiments of the invention, the cleavage of the mass tags from their associated probes must take place within the mass spectrometer. This cleavage is preferably effected by collision as discussed above. Collision based cleavage can be effected in the Electrospray Ion Source through manipulation of the Cone Voltage as discussed in more detail below. Alternatively, cleavage can take place in the mass analysis cell of an ion trap mass spectrometer or in a collision cell in a tandem mass spectrometer.

Inlet Systems:

In some embodiments of this invention a chromatographic or electrophoretic separation is preferred to reduce the complexity of the sample prior to analysis by mass spectrometry. A variety of mass spectrometry techniques are compatible with separation technologies particularly capillary zone electrophoresis and High Performance Liquid Chromatography (HPLC). The choice of ionisation source is limited to some extent if a separation is required as ionisation techniques such as MALDI and FAB (discussed below) which ablate material from a solid surface are less suited to chromatographic separations. For most purposes, it has been very costly to link a chromatographic separation in-line with mass spectrometric analysis by one of these techniques. Dynamic FAB and ionisation techniques based on spraying such as electrospray, thermospray and APCI are all readily compatible with in-line chromatographic separations and equipment to perform such liquid chromatography mass spectrometry analysis is commercially available.

Ionisation Techniques:

For many biological mass spectrometry applications so called 'soft' ionisation techniques are used. These allow large molecules such as proteins and nucleic acids to be ionised essentially intact. The liquid phase techniques allow large biomolecules to enter the mass spectrometer in solutions with mild pH and at low concentrations. A number of techniques are appropriate for use with this invention including but not limited to Electrospray Ionisation Mass Spectrometry (ESI-MS), Fast Atom Bombardment (FAB), Matrix Assisted Laser Desorption Ionisation Mass Spectrometry (MALDI MS) and Atmospheric Pressure Chemical Ionisation Mass Spectrometry (APCI-MS).

Electrospray Ionisation:

Electrospray Ionisation (ESI) requires that the dilute solution of the analyte molecule is 'atomised' into the spectrometer, i.e. injected as a fine spray. The solution is, for example, sprayed from the tip of a charged needle in a stream of dry nitrogen and an electrostatic field. The mechanism of ionisation is not fully understood but is thought to work broadly as follows. In a stream of nitrogen the solvent is evaporated. With a small droplet, this results in concentration of the analyte molecule. Given that most biomolecules have a net charge this increases the electrostatic repulsion of the dissolved molecule. As evaporation continues this repulsion ultimately becomes greater than the surface tension of the droplet and the droplet disintegrates into smaller droplets. This process is sometimes referred to as a 'Coulombic explosion'. The electrostatic field helps to further overcome the surface tension of the droplets and assists in the spraying process. The evaporation continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber by the use of electric fields that are set up by appropriately positioned electrodes. The polarity of the fields may be altered to extract either negative or positive ions. The potential difference between these electrodes determines whether positive or negative ions pass into the mass analyser and also the kinetic energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the electric field used to accelerate ions from the ionisation chamber it is possible to control the fragmentation of ions. This is advantageous when fragmentation of ions is to be used as a means of removing tags from a labeled biomolecule. Electrospray ionisation is particularly advantageous as it can be used in-line with liquid chromatography and capillary electrophoresis, referred to as Liquid Chromatography Mass Spectrometry (LC-MS) and Capillary Electrophoresis Mass Spectrometry (CE-MS) respectively.

Atmospheric Pressure Chemical Ionisation:

Atmospheric Pressure Chemical Ionisation (APCI) is similar to (ESI) in that a dilute solution of the analyte molecule can be 'atomised' or nebulised into the ion source at atmospheric pressure, however ionisation takes place by chemical ionisation. In APCI the ion source is filled with a bath gas that is subjected to a coronal discharge source which essentially generates a plasma ionising the bath gas, which in turn ionises the molecules that are sprayed into the ion source. APCI can also be coupled to laser desorption ionisation (Coon J. J. et al., Rapid Commun Mass Spectrom., 16(7): 681-685, "Atmospheric pressure laser desorption/chemical ionization mass spectrometry: a new ionization method based on existing themes." (2002)), which may also be advantageous in certain embodiments of this invention, particularly the microarray embodiments. In general APCI is a relatively mild technique appropriate for analysis of mass tags.

Matrix Assisted Laser Desorption Ionisation (MALDI):

MALDI requires that the biomolecule solution be embedded in a large molar excess of a photo-excitable 'matrix'. The application of laser light of the appropriate frequency results in the excitation of the matrix which in turn leads to rapid evaporation of the matrix along with its entrapped biomolecule. Proton transfer from the acidic matrix to the biomolecule gives rise to protonated forms of the biomolecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. Accelerating voltages can again be used to control fragmentation in variations of this technique, such as Post Source Decay. The use of laser desorption techniques is particularly compatible with applications of this invention where microarray are used to analyse CCPs with Microarray Address Sequences.

Fast Atom Bombardment:

Fast Atom Bombardment (FAB) has come to describe a number of techniques for vaporising and ionising relatively involatile molecules. In these techniques a sample is desorbed from a surface by collision of the sample with a high energy beam of xenon atoms or caesium ions. The sample is coated onto a surface with a simple matrix, typically a non volatile material, e.g. m-nitrobenzyl alcohol (NBA) or glycerol. FAB techniques are also compatible with liquid phase inlet systems—the liquid eluting from a capillary electrophoresis inlet or a high pressure liquid chromatography system pass through a frit, essentially coating the surface of the frit with analyte solution which can be ionised from the frit surface by atom bombardment.

Mass Analysers:

Fragmentation of peptides by collision induced dissociation is used in this invention to identify tags on proteins. Various mass analyser geometries may be used to fragment peptides and to determine the mass of the fragments.

MS/MS and MS" Analysis of Peptide Tandem Mass Tags:

Tandem mass spectrometers allow ions with a pre-determined mass-to-charge ratio to be selected and fragmented by collision induced dissociation (CID). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CID fragment series are denoted $a_n$, $b_n$, $c_n$, etc. for cleavage at the $n^{th}$ peptide bond where the charge of the ion is retained on the N-terminal fragment of the ion. Similarly, fragment series are denoted $x_n$, $y_n$, $z_n$, etc. where the charge is retained on the C-terminal fragment of the ion.

Trypsin and thrombin are favoured cleavage agents for tandem mass spectrometry as they produce peptides with basic groups at both ends of the molecule, i.e. the alpha-amino group at the N-terminus and lysine or arginine side-chains at the C-terminus. This favours the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of quadrupole based instruments the b-series of N-terminal fragments or the y-series of C-terminal fragments predominate. If doubly charged ions are analysed then both series are often detected. In general, the y-series ions predominate over the b-series.

In general peptides fragment via a mechanism that involves protonation of the amide backbone follow by intramolecular nucleophilic attack leading to the formation of a 5-membered oxazolone structure and cleavage of the amide linkage that was protonated (Schlosser A. and Lehmann W. D. J. Mass Spectrom. 35: 1382-1390, "Five-membered ring formation in unimolecular reactions of peptides: a key structural element controlling low-energy collision induced dissociation", 2000). FIG. 16a shows one proposed mechanism by which this sort of fragmentation takes place. This mechanism requires a carbonyl group from an amide bond adjacent to a protonated amide on the N-terminal side of the protonated amide to carry out the nucleophilic attack. A charged oxazolonium ion gives rise to b-series ions, while proton transfer from the N-terminal fragment to the C-terminal fragment gives rise to y-series ions as shown in FIG. 16a. This requirement for an appropriately located carbonyl group does not account for cleavage at amide bonds adjacent to the N-terminal amino acid, when the N-terminus is not protected and, in general, b-series ions are not seen for the amide between the N-terminal and second amino acid in a peptide. However, peptides with acetylated N-termini do meet the structural requirements of this mechanism and fragmentation can take place at the amide bond immediately after the first amino acid by this mechanism. Peptides with thioacetylated N-termini, will cleave particularly easily by the oxazolone mechanism as the sulphur atom is more nucleophilic than an oxygen atom in the same position. Fragmentation of the amide backbone of a peptide can also be modulated by methylation of the backbone. Methylation of an amide nitrogen in a peptide can promote fragmentation of the next amide bond C-terminal to the methylated amide and also favours the formation of b-ions. The enhanced fragmentation may be partly due to the electron donating effect of the methyl group increasing the nucleophilicity of the carbonyl group of the methylated amide, while the enhanced formation of b-ions may be a result of the inability of the oxazolonium ion that forms to transfer protons to the C-terminal fragment as shown in FIG. 16b. In the context of this invention thioacetylation of the N-terminus of a tag peptide can be used to enhance cleavage of the tag peptide at the next amide bond. Similarly, methylation of the nitrogen atom of an N-terminal acetyl or thioacetyl group will also enhance cleavage of the adjacent amide bond.

The ease of fragmentation of the amide backbone of a polypeptide or peptide is also significantly modulated by the side chain functionalities of the peptide. Thus the sequence of a peptide determines where it will fragment most easily. In general it is difficult to predict which amide bonds will fragment easily in a peptide sequence. This has important consequences for the design of the peptide mass tags of this invention. However, certain observations have been made that allow peptide mass tags that fragment at the desired amide bond to be designed. Proline, for example, is known to promote fragmentation at its N-terminal amide bond (Schwartz B. L., Bursey M. M., Biol. Mass Spectrom. 21:92, 1997) as fragmentation at the C-terminal amide gives rise to an energetically unfavourable strained bicyclic oxazolone structure. Aspartic acid also promotes fragmentation at its N-terminal amide bond. Asp-Pro linkages, however, are particularly labile in low energy CID analysis (Wysocki V. H. et al., J Mass Spectrom 35(12): 1399-1406, "Mobile and localized protons: a framework for understanding peptide dissociation." 2000) and in this situation aspartic acid seems to promote the cleavage of the amide bond on its C-terminal side. Thus proline, and asp-pro linkages can also be used in the tag peptides of this invention to promote fragmentation at specified locations within a peptide.

A typical tandem mass spectrometer geometry is a triple quadrupole which comprises two quadrupole mass analysers separated by a collision chamber, also a quadrupole. This collision quadrupole acts as an ion guide between the two mass analyser quadrupoles. A gas can be introduced into the collision quadrupole to allow collision with the ion stream from the first mass analyser. The first mass analyser selects ions on the basis of their mass/charge ration which pass through the collision cell where they fragment. The fragment ions are separated and detected in the third quadrupole. Induced cleavage can be performed in geometries other than tandem mass analysers. Ion trap mass spectrometers can promote fragmentation through introduction of a gas into the trap itself with which trapped ions will collide. Ion traps generally contain a bath gas, such as helium but addition of neon for example, promotes fragmentation. Similarly photon induced fragmentation could be applied to trapped ions. Another favorable geometry is a Quadrupole/Orthogonal Time of Flight tandem instrument where the high scanning rate of a quadrupole is coupled to the greater sensitivity of a reflectron TOF mass analyser to identify the products of fragmentation.

Conventional 'sector' instruments are another common geometry used in tandem mass spectrometry. A sector mass analyser comprises two separate 'sectors', an electric sector which focuses an ion beam leaving a source into a stream of ions with the same kinetic energy using electric fields. The magnetic sector separates the ions on the basis of their mass to generate a spectrum at a detector. For tandem mass spectrometry a two sector mass analyser of this kind can be used where the electric sector provide the first mass analyser stage, the magnetic sector provides the second mass analyser, with a collision cell placed between the two sectors. Two complete sector mass analysers separated by a collision cell can also be used for analysis of mass tagged peptides.

Ion Traps:

Ion Trap mass analysers are related to the quadrupole mass analysers. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device as the ions entering the trap are essentially cooled to the ambient temperature of the bath gas through collision with the bath gas. Collisions both increase ionisation when a sample is introduced into the trap and dampen the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. It is possible to retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS):

FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates' which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole, for example.

Analysis of TMT Labelled Oligonucleotide Probes by MS/MS:

In preferred embodiments of this invention, the circularised probes are identified by copying successfully circularised probes onto a solid phase support using Linear Rolling Circle Replication. The captured multimeric repeats of the circularised probe sequences are then probed with oligonucleotides conjugated to Tandem Mass Tags (TMTs).

After cleavage of the TMTs from their oligonucleotides, the TMTs are isolated and injected into the ion source of an appropriate MS/MS instrument. Typically Electrospray Ionisation (ESI) or Atmospheric Pressure Chemical Ionisation (APCI) sources will be used. The tags can then be detected by selected reaction monitoring with a triple quadrupole for example. Briefly, the first quadrupole of the triple quadrupole is set to let through ions whose mass-to-charge ratio corresponds to that of the parent tag mass of interest. The selected parent tag ions are then subjected to collision induced dissociation (CID) in the second quadrupole. Under the sort of conditions used in the analysis of peptides the ions will fragment mostly at the amide bonds in the molecule the tag fragment. Although the tags all have the same mass, the terminal portion is different because of differences in the substituents on either side of the amide bond. Thus the markers can be distinguished from each other. The presence of the marker fragment associated with a parent ion of a specific mass should identify the tag ion and consequently its associated oligonucleotide.

Illustration of the Invention

In order to demonstrate the invention further, the following three illustrations show how the techniques described herein may be used in the detection of target sequences.

Protocol 1—Detection of HIV Mutations.

There are about 16 approved drugs (Shafer R. W., Clin Microbiol Rev. 15(2):247-277, "Genotypic testing for human immunodeficiency virus type 1 drug resistance." 2002) in use for treatment of human immunodeficiency virus type 1 (HIV-1). These drugs belong to three mechanistic classes: protease inhibitors, nucleoside and nucleotide reverse transcriptase (RT) inhibitors, and non-nucleoside RT inhibitors. New drugs based on novel mechanisms, such as cell entry inhibitors and integrase inhibitors are under development (Gulick R. M., Clin Microbiol Infect. 9(3):186-193, "New antiretroviral drugs." 2003). The reason for this proliferation of drugs is due to the ability of HIV-1 to evolve resistance to these drugs. Resistance is caused by mutations in the target proteins, which are the protease and RT enzymes for the existing approved drugs. Drug resistance mutations arise most often in treated individuals, as a result of selective drug pressure in the presence of incompletely suppressed virus replication.

HIV-1 isolates with drug resistance mutations, however, may also be transmitted to newly infected individuals. This means that it is extremely important to be able to detect mutations present in the virus population in a patient. Although the mechanism of mutation is not fully established, it is believed that there is a high natural level of mutation in the HIV-1 virus and that essentially all possible mutations are generated in the virus population at some point. Drug therapies select for particular resistant variant which gradually become predominant. It is this process of change in the predominance of particular HIV-1 variant that leads to resistance and failure of therapy. It is thus essential, not only to be able to identify HIV-1 mutations but to accurately quantify their presence.

HIV-1 mutations are, by convention, defined as amino acid substitutions with reference to a specific sequence referred to as the subtype B consensus sequence, which can be obtained from the Human Immunodeficiency Virus Reverse Transcriptase and Protease Sequence Database (Shafer R. W. et al., Nucleic Acids Res. 27(1):348-352, 1999) maintained by Stanford University.

There are currently, approximately 80 amino acids in the HIV genome in which substitutions are known to result in drug resistance. At some of these 80 amino acid positions, more than one amino acid can be substituted into the sequence, meaning that more than 100 amino acid substitutions need to be detected in an HIV-1 assay, requiring the ability to resolve 180 or more probes for each amino acid. Since each amino acid can be produced by more than one codon, this corresponds to the possibility of up to 4 distinct codons for each amino acid probe at the nucleic acid level. Not all of these codon changes occur at an appreciable level in vivo and since it is the functional change, i.e. the amino acid change that needs to be detected, probes for different codons for the same amino acid could be labeled with the same mass tag or could use the same Probe Identification sequence.

In principle, however, all possible changes could be tested for. In addition, certain substitutions are functionally equivalent, leucine and isoleucine are often interchangeable. Similarly, valine is often interchangeable with leucine and isoleucine. This means that LCPs to detect functionally equivalent substitutions could use the same mass tag or the same Probe Identification sequence too.

Bi-Allelic LCPs

TABLE 1

Components of a two probe set for the detection of the M184V mutation in the HIV-1 reverse transcriptase gene using linear Rolling Circle Replication.

| Component | Probe 1 (Met) | Probe 2 (Val) |
|---|---|---|
| 5' Target Recognition Sequence | ATGTATTGATAGATA | ACGTATTGATAGATA |
| Primer Binding Sequence | ATGTTAAGTGACCGG CAGCA | ATGTTAAGTGACCGGCAG CA |
| Probe Identification Sequence | GATTTGATTAGATTTG GTAA | AGTAATGTGATTTGATAA AG |
| 3' Target Recognition Sequence | ACATATAAATCATCC | ACATATAAATCATCA |

To illustrate the design of probes for an HIV assay, probes are shown in Table 1 that have been designed to detect the M184V mutation in reverse transcriptase that gives rise to AZT resistance (Shirasaka T. et al., Proc Natl Acad Sci USA. 90(2):562-566, "Changes in drug sensitivity of human immunodeficiency virus type 1 during therapy with azidothymidine, dideoxycytidine, and dideoxyinosine: an in vitro comparative study." 1993). These probes are designed for amplification by linear Rolling Circle Replication and comprise four components: a 5' Target Recognition Sequence, a Primer Binding Sequence, a Probe Identification Sequence and 3' Target Recognition Sequence. The complete 70 base sequences of Linear Circularising Probes 1 and 2 are shown below and would be phosphorylated at the 5' hydroxyl group:

LCP1:
5'-Atgtattgatagataa*tgttaagtgac
cggcagc*a*gatttgattaga
tttggtaa*acatataaatcatcc-3'

(TRS1 and TRS2 in bold, PBS in italics)

LCP2:
5'-Acgtattgatagataagtgaccggcagcaagtaatgtgatt
tgataaagacatataaacatca-3'

The two Target Recognition Sequences in Table 1 are each 15 bases in length. It can also be seen from Table 1 that the same Primer Binding Sequence (PBS) is used for both probes and that this PBS will bind to a 20-mer primer with the following sequence, which is preferably biotinylated:

Primer:
5'-TGCTGCCGGTCACTTAACAT-3'

Conversely, it can be seen from Table 1 that a different 20-mer Probe Identification Sequence is used to identify each probe. The design of these sequences is based on the disclosure of Brenner et al. in U.S. Pat. No. 5,846,719, which provides a convenient method for designing sets of oligonucleotide tags which will have a minimal ability to cross-hybridise with each other's target sequences. The corresponding Probe Detection Sequences that are used to detect the Probe Identification Sequences will have the same sequence as the Probe Identification Sequence as they must bind to the complement of the Probe Identification Sequence that will be produced by linear RCR of CCPs formed from LCPs that correctly bind their targets. Thus the Probe Identification Sequence in LCP1 can be detected after linear RCR by the following Probe Detection Sequence (PDS):

PDS1:
5'-gatttgattagatttggtaa-3'

Similarly, the Probe Identification Sequence in LCP2 can be detected after linear RCR by this Probe Detection Sequence:

PDS2:
5'-agtaatgtgatttgataaag-3

The PDS sequences are linked to a mass tag, preferably by a photocleavable linker as disclosed in WO 97/27327 or a collision cleavable linker as disclosed in WO98/31830. However, it is preferred that the mass tags comprise a short peptide mass tag as disclosed in WO 03/025576.

Redundant LCPs:

Table 1 and probes LCP1 and LCP2 illustrate the basic design of a Linear Circularising Probe to assay for an amino acid substitution in the HIV-1 reverse transcriptase gene. However, a number of different nucleic acid changes can give rise to the same amino acid change. Thus multiple LCP sequences could be necessary to detect all possible variants of a sequence. Since all these sequences give rise to the same amino acid change they could all be identified by the same mass tag or Probe Identification Sequence. For the M184V mutation this would result in a set of probes as shown in Table 2 corresponding to the probe sets LCP3 and LCP4 shown below.

TABLE 2

Components of a two probe set for the detection of the M184V mutation in the HIV-1 reverse transcriptase gene using linear Rolling Circle Replication where all possible codons are detected.

| Component | Probe 3 (Met) | Probe 4 (Val) |
|---|---|---|
| 5' Target Recognition Sequence | ATGTATTGATAGATA | ACGTATTGATAGATA (1) |
| | | CCGTATTGATAGATA (2) |
| | | TCGTATTGATAGATA (3) |
| | | GCGTATTGATAGATA (4) |
| Primer Binding Sequence | ATGTTAAGTGACCGG CAGCA | ATGTTAAGTGACCGGCAG CA |
| Probe Identification Sequence | GATTTGATTAGATTT GGTAA | AGTAATGTGATTTGATAA AG |
| 3' Target Recognition Sequence | ACATATAAATCATCC | ACATATAAATCATCA (1) |
| | | ACATATAAATCATCA (2) |
| | | ACATATAAATCATCA (3) |
| | | ACATATAAATCATCA (4) |

It can be seen that only one probe is required for the detection of an internal methionine residue as there is only one codon in the human code for internal methionine residues. Valine, however can be encoded by four different codons and so four different probes are need for the detection of nucleic acid mutations that cause valine to be substituted into a protein. Thus, the complete 70 base sequences of Linear Circularising Probes 3 and 4 are shown below and would be phosphorylated at the 5' hydroxyl group:

LCP3:
5'-Atgtattgatagataatgttaagtgaccggcagcagatttgattaga
tttggtaaacatataaatcatcc-3'

LCP4:
5'-Acgtattgatagataatgttaagtgaccggcagcaagtaatgtgatt
tgataaagacatataaatcatca-3'

5'-Ccgtattgatagataatgttaagtgaccggcagcaagtaatgtgatt
tgataaagacatataaacatca-3'

5'-Tcgtattgatagataatgttaagtgaccggcagcaagtaatgtgatt
tgataaagacatataaatcatca-3'

5'-Gcgtattgatagataatgttaagtgaccggcagcaagtaatgtgatt
tgataaagacatataaatcatca-3'

Since only one codon needs to be tested for methionine LCP3 is the same as LCP1 but LCP4 comprises four different probes to detect all nucleic acid changes that encode for valine, all identified by the same Probe Identification Sequence.

LCPs PCR and Hyper-Branching RCR:

The sequences for LCPs 1 to 4 are all designed for linear Rolling Circle Replication and require only one primer sequence. However, for PCR amplification or for hyper-branching RCR, two primers are required and the corresponding Primer Binding Sequences must be incorporated into the corresponding LCPs.

TABLE 3

Components of a two probe set for the detection of the M184V mutation in the HIV-1 reverse transcriptase gene for PCR amplification or Hyper-Branching Rolling Circle Replication.

| Component | Probe 5 (Met) | Probe 6 (Val) |
|---|---|---|
| 5' Target Recognition Sequence | ATGTATTGATAGATA | ACGTATTGATAGATA |
| Primer Binding Sequence 1 | TGCTTTCCAGACCGT CCATCA | TGCTTTCCAGACCGT CCATCA |
| Probe Identification Sequence | gatttgattagatttggtaa | AGTAATGTGATTTGAT AAAG |
| Primer Binding Sequence 2 | ggtgcctgtgcattgcctgcc | GGTGCCTGTGCATTG CCTGCC |
| 3' Target Recognition Sequence | ACATATAAATCATCC | ACATATAAATCATCA |

It can be seen from Table 3 that for PCR or Hyper-branching Rolling Circle Replication, two primers are needed and that the same Primer Binding Sequences (PBS) are used for both probes. Primer 1, is preferably biotinylated. Again, the PBS sites will bind to 20-mer primers with the following sequences:

```
Primer 1:
5'-gatggacggtctggaaagcaa-3'

Primer 2:
5'-ggtgcctgtgcattgcctgcc-3'
```

Note that Primer 2 has the same sequence as the PBS as it is designed to bind to the complementary strand generated by Primer 1. Thus, the complete 90 base sequences of the example Linear Circularising Probes for detecting the M184V mutation in the HIV-1 reverse transcpriptase gene are shown below and would be phosphorylated at the 5' hydroxyl group:

```
LCP5:
5'-ATGTATTGATAGATATGCTTTCCAGACCGTCCATCAGATTTGATTAG
ATTTGGTAAGGTGCCTGTGCATTGCCTGCCACATATAAATCATCC-3'

LCP6:
5'-AcgtattgatagataTGCTTTCCAGACCGTCCATCAagtaatgtgat
ttgataaagggtgcctgtgcattgcctgccacatataaatcatca-3'
```

Since PCR amplification and hyper-branching RCR generate sense and antisense copies of any CCPs that form, the Probe Detection Sequences can be designed to bind to either the sense or antisense amplification products. Thus the Probe Identification Sequence in LCP5 can be detected after amplification by PDS1 or by the following Probe Detection Sequence (PDS):

```
PDS3:
5'-TTACCAAATCTAATCAAATC-3'
```

Similarly, the Probe Identification Sequence in LCP6 can be detected after amplification by PDS2 or by this Probe Detection Sequence:

```
PDS4:
5'-CTTTATCAAATCACATTACT-3'
```

The Assay:

The first step in a viral load or genotyping assay would be the extraction of the RNA from the source biological sample, which is typically blood plasma for an HIV assay. This can be done using a QIAamp Viral RNA kit from QIAgen (Hilden, Germany) following the manufacturer's instructions. For a comprehensive review of viral RNA extraction methods see Verhofstede C. et al., J Virol Methods. 60(2):155-159, "Isolation of HIV-1 RNA from plasma: evaluation of eight different extraction methods." 1996 and Fransen K. et al., J Virol Methods. 76(1-2):153-157, "Isolation of HIV-1 RNA from plasma: evaluation of seven different methods for extraction (part two)." 1998.

After RNA extraction the RNA is assayed with the Linear Circularising Probes (LCP1 and LCP2) comprised of the components shown in table 1. Alternatively, if all possible codons are to be detected then LCPs comprising of the components shown in table 2 would be used (LCP3 and LCP4). If PCR or hyper-branching RCR is to be used later in the assay then Linear Circularising Probes comprised of the components shown in table 3 would be used (LCP5 and LCP6). Appropriate assay conditions for RNA mediated ligation of LCPs with T4 RNA ligase are disclosed by Nilsson M. et al., Nat. Biotechnol. 18(7):791-793, "Enhanced detection and distinction of RNA by enzymatic probe ligation." 2000 and Nilsson M. et al., Nucleic Acids Res. 29(2):578-581, "RNA-templated DNA ligation for transcript analysis." 2001.

After ligation of LCPs to form CCPs the CCPs are amplified. Amplification is generally inhibited if the CCPs remain associated with their targets. Since HIV-1 is an RNA virus, the RNA can be selectively degraded by addition of RNAse H under hybridizing conditions. The free CCPs are then available for unrestricted amplification.

Methods for amplification of circular oligonucleotide probes are disclosed by Baner J. et al. (Nucleic Acids Res. 26(22):5073-5078, "Signal amplification of padlock probes by rolling circle replication." 1998) for example, or Zhang D. Y. et al. (Gene. 274(1-2):209-216, "Detection of rare DNA targets by isothermal ramification amplification." 2001) or Hardenbol et al. (Nature Biotechnology 21(6) pages 673-678, 2003). The protocol disclosed by Zhang et al. uses a second primer sequence to effect a form of hyper-branching RCR and would thus require LCPs with the components shown in table 3 to be used. Similarly, the protocol disclosed by Hardenbol et al. uses two primers to amplify CCPs by PCR. In the Hardenbol protocol, prior to PCR the CCPs are linearised. For the purposes of this example, the protocols disclosed in these publications would be modified such that the primer for initiating rolling circle replication would be biotinylated. This would allow a further step in the process to be carried out which is the capture of the linear tandem repeat RCR product onto an avidinated support such as the BioMag Nuclease-Free Streptavidin from Qiagen (Hilden, Germany), Avidinated Magnetic Porous Glass (MPG) particles from CPG Inc (Lincoln Park, N.J., USA) or Avidin Magnetic Particles from Spherotech, Inc (Libertyville, Ill., USA). Magnetic particles are preferred for ease of handling with automated instrumentation such as the Kingfisher magnetic particle processor instruments (Thermo Electron Corporation, Waltham, Mass., USA). The captured RCR product can then be washed on the beads allowing unreacted probes and other unwanted reagents to be washed away.

The captured RCR products are then probed with mass tagged Probe Detection Sequences, PDS1 and PDS2. The probes are added in a mass spectrometry compatible hybridization enhancing buffer such as those disclosed in WO 97/14815 or WO 98/13527 which comprise volatile salts. After allowing hybridization to proceed for a suitable period of time, unhydridised PDS sequences are washed away. The tags are then analysed. If a photocleavable linker has been used to link the mass tags to the PDS oligonucleotides, then cleavage and analysis of the tags can be effected according to the disclosure of WO 97/27327. If a collision cleavable linker has been used then the correctly hybridised oligonucleotides must be denatured from the captured RCR products, by heating for example and the released PDS oligonucleotides are injected into the ion source of an electrospray mass spectrometer and the tags are cleaved by increasing the cone voltage in the electrospray ion source as disclosed in WO98/31830. If peptide tags of the kind disclosed in WO 03/025576, then it will be necessary to carry out the sort of MS/MS analysis disclosed in this patent application.

In this example, probes for a single mutation have been illustrated. The references cited all disclose the use of multiple probes and the methods above are applicable to assays which comprise numerous distinct LCPs. As long as these are uniquely identifiable, and U.S. Pat. No. 5,846,719 discloses methods for designing large arrays of oligonucleotide tags and tag complements that can be used for LCP identification, it will be possible for one of ordinary skill in the art to adapt the above example to more highly multiplexed assays.

Protocol 2—Detection of BRCA1 Gene Mutation.

Breast cancer is the most common cancer to affect women and it is believed that there is a strong genetic basis for the disease. Research has shown up to 5% of breast and ovarian cancers are caused by mutations in two genes alone, dubbed BRCA1 and BRCA2 (Ponder B A. Biochem Soc Symp. 63:223-230, "Inherited predisposition to breast cancer." 1998). Recent research has uncovered more than 150 nucleotide substitutions in the BRCA1 gene alone (Stenson P. D. et al., Hum Mutat. 21(6):577-581, "Human Gene Mutation Database (HGMD): 2003 update." 2003). Comprehensive screening of all these mutations in an affordable assay is highly desirable to allow accurate determinations of the risk of developing the disease, and in patients with the disease, to allow determination of the most appropriate treatment.

TABLE 4

Components of a two probe set for the detection of the G255A mutation in the BRCA1 gene nucleotide sequence using linear Rolling Circle Replication.

| Component | Probe 7 | Probe 8 |
| --- | --- | --- |
| 5' Target Recognition Sequence | TTTGTGGAGACAGGT | TTTGTGGAGACAGGT |
| Primer Binding Sequence | ATGTTAAGTGACCGG CAGCA | ATGTTAAGTGACCCGCAG CA |
| Probe Identification Sequence | GATTTGATTAGATTTG GTAA | AGTAATGTGATTTGATAA AG |
| 3' Target Recognition Sequence | AATATGTGGTCACAC | AATATGTGGTCACAT |

To illustrate the design of probes for a BRCA1 assay, probe components are shown in Table 4 that have been designed to detect a single nucleotide substitution that is known to occur in the BRCA1 gene. This mutation is listed in dbSNP (Wheeler D. L. et al., Nucleic Acids Res. 32 Database issue: D35-40, "Database resources of the National Center for Biotechnology Information: update." 2004) under the accession rs1800062. Two variants of this mutation exist in which a G is replaced with an A residue. The pair of probes for this mutation comprise four components: a 5' Target Recognition Sequence, a Primer Binding Sequence, a Probe Identification Sequence and 3' Target Recognition Sequence. The complete 70 base sequences of Linear Circularising Probes 7 and 8 are shown below and would be phosphorylated at the 5' hydroxyl group:

LCP7:
5'-TTTGTGGAGACAGGTatgttaagtgaccggcagcagatttgattaga tttggtaaAATATGTGGTCACAC-3'

LCP8:
5'-TTTGTGGAGACAGGTatgttaagtgaccggcagcaagtaatgtgatt tgataaagAATATGTGGTCACAT-3'

The other features of this probe are the same as those for the probes shown in Table 1 for Example 1.

The Assay:

The first step in a genotyping assay of this kind would be the extraction genomic DNA from the source biological sample, which could be a cheek swab or a blood sample. This extraction can be done using a QIAamp Blood kit from QIAgen (Hilden, Germany) following the manufacturer's instructions.

After genomic DNA extraction the DNA is assayed with the Linear Circularising Probes (LCP7 and LCP8) comprised of the components shown in table 4. Appropriate assay conditions for DNA mediated ligation of LCPs are disclosed by Baner J. et al. (Nucleic Acids Res. 26(22):5073-5078, "Signal amplification of padlock probes by rolling circle replication." 1998).

Methods for amplification of circular oligonucleotide probes are also disclosed by Baner J. et al. PCR or hyperbranching RCR can also be used with this sort of assay but would require an additional Primer Binding Site added to the LCP7 and LCP8 sequences. For the purposes of this example, the protocol disclosed by Baner J. et al. would be modified such that the primer for initiating rolling circle replication would be biotinylated. This would allow a further step in the process to be carried out which is the capture of the linear tandem repeat RCR product onto an avidinated support as discussed in Example 1. The captured RCR product can then be washed on the beads allowing unreacted probes and other unwanted reagents to be washed away.

The captured RCR products are then probed with mass tagged Probe Detection Sequences, PDS1 and PDS2. The probes are added in a mass spectrometry compatible hybridization enhancing buffer such as those disclosed in WO 97/14815 or WO 98/13527, which comprise volatile salts. After allowing hybridization to proceed for a suitable period of time, unhydridised PDS sequences are washed away. The tags are then analysed. If a photocleavable linker has been used to link the mass tags to the PDS oligonucleotides, then cleavage and analysis of the tags can be effected according to the disclosure of WO 97/27327. If a collision cleavable linker has been used then the correctly hybridised oligonucleotides must be denatured from the captured RCR products, by heating for example and the released PDS oligonucleotides are injected into the ion source of an electrospray mass spectrometer and the tags are cleaved by increasing the cone voltage in the electrospray ion source as disclosed in WO98/31830. If peptide tags of the kind disclosed in WO 03/025576, then it will be necessary to carry out the sort of MS/MS analysis disclosed in this patent application.

Protocol 3—Leukemia Diagnosis

Leukemia is a cancer of the immune system's T-cells that is characterised by a number of genetic translocations that give rise to abnormal protein expression. Profiling of T-cell mRNA expression is emerging as a useful tool in classifying leukemia's according to the translocations that are present (Schoch C. et al., Proc Natl Acad Sci USA. 99(15):10008-13. Epub 2002 July 08, "Acute myeloid leukemias with reciprocal rearrangements can be distinguished by specific gene expression profiles." 2002; Kohlmann A. et al., Genes Chromosomes Cancer. 37(4):396-405, "Molecular characterization of acute leukemias by use of microarray technology." 2003). The ability to perform these sorts of classifications is extremely useful in determining appropriate treatment regimes for patients to ensure the best possible outcome from treatment (Roche-Lestienne C. and Preudhomme C., Semin Hematol. 40(2 Suppl 2):80-82, "Mutations in the ABL kinase domain pre-exist the onset of imatinib treatment." 2003).

To illustrate the design of Linear Circularising Probes for a leukemia T-cell expression profiling assay, a set of probes is shown in Table 5 that has been designed to detect the b3a2 variant of the t(9;22) translocation (Melo J. V., Baillieres Clin Haematol. 10(2):203-222, "BCR-ABL gene variants." 1997) that is the classic signature of Chronic Myeloid Leukemia (CML) and the corresponding normal sequences that give rise to the gene fusion. The t(9;22) translocation is the result of the fusion of two genes, ABL and BCR, that normally reside on chromosomes 9 and 22 respectively. Transcription and translation of this fusion gene produces an abnormal protein dubbed BCR-ABL that can transform non-proliferative cells into cancerous cells. These LCPs are designed for amplification by linear Rolling Circle Replication followed by detection on a microarray. The LCPs comprise five components: a 5' Target Recognition Sequence, a Primer Binding Sequence, a Microarray Address Sequence, a Probe Identification Sequence and 3' Target Recognition Sequence. The complete 90 base sequences of Linear Circularising Probes 9, 10 and 11 are shown below and would be phosphorylated at the 5' hydroxyl group:

LCP9:
5'-TTGAACTCTGCTTAAatgttaagtgaccggcagcaGTAAAGTAGATT
ATGTTAGAgatttgattagatttggtaaCAAACCAGTACTTAC-3'

LCP10:
5'-CTTCCAGATAACAGCatgttaagtgaccggcagcaTGATTTTGATGT
GTAAGATTagtaatgtgatttgataaagGCCGCTGAAGGGCTT-3'

LCP11:
5'-TTGAACTCTGCTTAAatgttaagtgaccggcagcaTAGAGTAAATGA
AAAGTGATTTTGTAGATTTGAGTAAGTAGCCGCTGAAGGGCTT-3'

The two Target Recognition Sequences in Table 5 are each 15 bases in length. It can also be seen from Table 5 that the same Primer Binding Sequence (PBS) is used for all three probes and that this PBS will bind to a 20-mer primer with the following sequence, which is preferably biotinylated:

TABLE 5

Components of a two probe set for the detection of the t(9;22) translocation resulting in the formation of the b3a2 variant of the BCR-ABL fusion gene using linear Rolling Circle Replication and microarray based detection.

| Component | LCP9 (BCR) | LCP10 (ABL) | LCP11 (BCR-ABL) |
|---|---|---|---|
| 5' Target Recognition Sequence | TTGAACTCTGCTTAA | CTTCCAGATAACAGC | TTGAACTCTGCTTAA |
| Primer Binding Sequence | ATGTTAAGTGACCGGC AGCA | ATGTTAAGTGACCGGC AGCA | ATGTTAAGTGACCGGC AGCA |
| Microarray Address Sequence | GTAAAGTAGATTATGT TAGA | TGATTTTGATGTGTAA GATT | TAGAGTAAATGAAAAG TGAT |
| Probe Identification Sequence | GATTTGATTAGATTTG GTAA | AGTAATGTGATTTGAT AAAG | TTTGTAGATTTGAGTA AGTA |
| 3' Target Recognition Sequence | CAAACCAGTACTTAC | GCCGCTGAAGGGCTT | GCCGCTGAAGGGCTT |

Primer:
5'-TGCTGCCGGTCACTTAACAT-3'

Conversely, it can be seen from Table 5 that a different 20-mer Probe Identification Sequence is used to identify each probe in the same way as the probes designed for linear RCR in Example 1. Thus PDS1 and PDS2, from Example 1, will identify LCP9 and LCP10 respectively. LCP11 would bind to a third PDS sequence as below:

PDS3:
5'-TTTGTAGATTTGAGTAAGTA-3'

These PDS sequences would be linked to a mass tag as discussed in Examples 1 and 2. However, one difference between Examples 1 and 2 and this example is that for a microarray based detection it would not be useful to use an electrospray cleavable linker and a photocleavable linker would be preferred.

The Assay:

The first step in a gene expression profiling assay would be the extraction of the mRNA from the source biological sample. The source biological sample comprises T-cells from blood for a Leukemia test. The extraction of mRNA from T-cells can be done using a QuickPrep Micro mRNA Purification Kit (Amersham Pharmacia Biotech, Uppsala, Sweden) or using an RNeasy Kit (Qiagen, Hilden, Germany) following the manufacturer's instructions.

After RNA extraction the RNA is assayed with the Linear Circularising Probes (LCP9, LCP10 and LCP11) comprised of the components shown in table 5. Appropriate assay conditions for RNA mediated ligation of LCPs with T4 RNA ligase are disclosed by Nilsson M. et al., Nat Biotechnol. 18(7):791-793, "Enhanced detection and distinction of RNA by enzymatic probe ligation." 2000 and Nilsson M. et al., Nucleic Acids Res. 29(2):578-581, "RNA-templated DNA ligation for transcript analysis." 2001.

After ligation of LCPs to form CCPs the CCPs are amplified. Amplification is generally inhibited if the CCPs remain associated with their targets. As discussed in Example 1, the mRNA can be selectively degraded by addition of RNAse H under hybridizing conditions. The free CCPs are then available for unrestricted amplification.

Methods for amplification of circular oligonucleotide probes using linear RCR are disclosed by Baner J. et al. (Nucleic Acids Res. 26(22):5073-5078, "Signal amplification of padlock probes by rolling circle replication." 1998) which would require that the CCPs are contacted with the Primer sequence complementary to the Primer Binding Site in LCPs 9, 10 and 11. The linear RCR products generated by the primer extension reaction would then by hybridised to an array comprising oligonucleotides that have the same sequences as the Microarray Address Sequences that were incorporated into LCP9, LCP10 and LCP11, so that the microarray sequences can bind to the complement of the Microarray Address Sequences that would be generated in the RCR product. Methods for hybridizing amplification products of CCPs to microarrays are provided by Baner J. et al. (Nucleic Acids Res. 31(17):e103, "Parallel gene analysis with allele-specific padlock probes and tag microarrays." 2003).

In an alternative approach linear RCR is performed on the microarray surface itself using the sequence on the array that is complementary to the Microarray Address Sequence as the RCR initiating primer. Methods for initiating RCA from a tethered oligonucleotide are provided by Lizardi P. M. et al. (Nat Genet. 19(3):225-32. "Mutation detection and single-molecule counting using isothermal rolling-circle amplification." 1998). In this case the microarray should be comprised of oligonucleotides whose sequences are complementary to the Microarray Address Sequences present in LCP9, LCP10 and LCP11. In this situation, the Primer Binding Sequence could be omitted from the probes used in the assay.

The captured RCR products on the microarray surface are then probed with mass tagged Probe Detection Sequences, PDS1, PDS2 and PDS3. The probes are added in a mass spectrometry compatible hybridization enhancing buffer such as those disclosed in WO 97/14815 or WO 98/13527 which comprise volatile salts. After allowing hybridization to proceed for a suitable period of time, unhydridised PDS sequences are washed away. The tags are then analysed. With a photocleavable linker connecting the mass tags to the PDS oligonucleotides, cleavage and analysis of the tags can be effected according to the disclosure of WO 97/27327. If peptide tags of the kind disclosed in WO 03/025576, then it will be necessary to carry out the sort of MS/MS analysis disclosed in this patent application. For purposes of this example, an Atmospheric Pressure MALDI ion source linked to an Ion Trap mass spectrometer would be appropriate. Such equipment is available from Agilent (Palo Alto, Calif., USA) or Thermo Finnigan (San Jose, Calif., USA). In a MALDI ion trap instrument, the tags would be sequentially laser desorbed from each location on the array In this example, probes for detection of a single mRNA translocation have been illustrated. These probes are designed around the translocation site. The probes do not represent a complete assay for leukemia translocations. The probes above can only indicate the presence or absence of the b3a2 variant of the t(9;22) translocation. Further probes would be required to classify all the possible t(9;22) translocation variants. In most of the references cited, the use of multiple probes is discussed and the methods above are applicable to assays which comprise numerous distinct LCPs. As long as these are uniquely identifiable by a unique combination of Probe Detection Sequences and Microarray Address Sequences, it will be possible for one of ordinary skill in the art to adapt the above example to more highly multiplexed assays. As discussed above, U.S. Pat. No. 5,846,719 discloses methods for designing large arrays of oligonucleotide tags and tag complements that can be used for LCP identification as both Probe Identification Sequences and as Microarray Address Sequences.

The invention claimed is:

1. A method of detecting the presence of a target nucleic acid in a sample, which method comprises a) contacting the sample, under hybridizing conditions, with a probe for said target nucleic acid, wherein said probe comprises two terminal nucleic acid target recognition sequences that are complementary to and capable of hybridizing to two neighbouring regions of the target sequence, and wherein the probe further comprises a probe identification sequence and a pair of primer binding sequences;

b) covalently connecting the ends of the hybridized probe with each other to form a circularized-probe, which interlocks with the target strand through catenation;

c) cleaving the circularized probe such that the opened probe has the primer binding sequences oriented to enable polymerase chain reaction amplification of the probe identification sequence;

d) hybridizing a probe detection oligonucleotide to the probe identification sequence present in the said probe, where the probe detection oligonucleotide is cleavably linked to a mass tag;

e) performing a primer extension reaction by providing a primer capable of hybridizing to the primer binding sequence upstream of the probe identification sequence and extending said primer with a polymerase having 5' exonuclease activity, so as to cleave the mass tag from the probe detection oligonucleotide;

f) detecting the mass tag by mass spectrometry; and g) detecting the presence of a target nucleic acid in the sample.

2. The method of claim 1 wherein the primer extension reaction is part of a polymerase chain reaction.

3. The method of claim 1 wherein the circularized probe is cleaved by hybridizing an oligonucleotide to the probe to form a type II restriction endonuclease recognition site, and cleaving the probe with a type II restriction endonuclease which recognises the site formed.

4. A method according to claim 1 wherein the two neighbouring regions of the target sequence are immediately adjacent to each other.

5. A method according to claim 1 wherein the two neighbouring regions of the target sequence are separated by a gap, and wherein covalent connection of the sequences is performed by providing an oligonucleotide capable of hybridising to the sequence between the neighbouring regions of the target sequence, and ligating said oligonucleotide to the terminal nucleic acid recognition sequences.

6. A method according to claim 1 wherein the two neighbouring regions of the target sequence are separated by a gap, and wherein covalent connection of the sequences is performed by providing a gap-filling polymerase and one or more nucleotide triphosphates to extend the 3' terminal nucleic acid target recognition sequence of the probe to fill the gap, and ligating the terminal nucleic acid recognition sequences.

7. A method according to claim 1, wherein the sample is contacted with two or more different probes capable of binding different alleles of the target sequence, under conditions which a probe complementary for an allele present in the sample will form a circularized probe and a probe not complementary for an allele present in the sample will not form a circularised probe, wherein each probe comprises a different probe identification sequence, and wherein the method includes the step of separating circularized probes from non-circularized probes.

* * * * *